(12) United States Patent
Zhang et al.

(10) Patent No.: US 8,614,333 B2
(45) Date of Patent: Dec. 24, 2013

(54) ACENAPHTHO HETEROCYCLIC COMPOUND AND APPLICATION THEREOF

(75) Inventors: Zhichao Zhang, Dalian (CN); Guiye Wu, Dalian (CN)

(73) Assignee: Dalian University of Technology, Dalian, Liaoning (CN)

( * ) Notice: Subject to any disclaimer, the term of this patent is extended or adjusted under 35 U.S.C. 154(b) by 0 days.

(21) Appl. No.: 13/810,901

(22) PCT Filed: Jul. 27, 2011

(86) PCT No.: PCT/CN2011/077682
§ 371 (c)(1),
(2), (4) Date: Jan. 18, 2003

(87) PCT Pub. No.: WO2012/013147
PCT Pub. Date: Feb. 2, 2012

(65) Prior Publication Data
US 2013/0123492 A1    May 16, 2013

(30) Foreign Application Priority Data

| Jul. 28, 2010 | (CN) | .................. PCT/CN2010/075521 |
| Jul. 11, 2011 | (CN) | .......................... 2011 1 0191880 |
| Jul. 11, 2011 | (CN) | .......................... 2011 1 0191883 |

(51) Int. Cl.
C07D 209/80    (2006.01)
C07D 417/10    (2006.01)

(52) U.S. Cl.
USPC ............................................. 548/426; 544/60

(58) Field of Classification Search
USPC ............................................. 548/426; 544/60
See application file for complete search history.

(56) References Cited

U.S. PATENT DOCUMENTS

2011/0251188 A1    10/2011    Zhang et al.

FOREIGN PATENT DOCUMENTS

| CN | 1304370 C | 3/2007 |
| CN | 101423491 A | 5/2009 |
| CN | 101633637 A | 1/2010 |
| WO | 2010054575 A1 | 5/2010 |

OTHER PUBLICATIONS

Liu et al. Bioorganic & Medicinal Chemistry (2006), 14(13), 4639-4644.*
Intercalation, Cytotoxicity, and Molecular Modeling of Acenaphtho[1, 2-b]pyrrole Chromophores as a New Family of Antitumor Agents, Zhang Zhi-chao, et al., Chem. Res. Chinese Universities, 24(4), 449-453. (2008).
3-Thiomorpholin-8-oxo-8H-acenaphtho[1,2-b]pyrrole-9-carbonitrile (S1) Based Molecules as Potent, Dual Inhibitors of B-Cell Lymphoma 2 (Bcl-2) and Myeloid Cell Leukemia Sequence 1 (Mcl-1): Structure-Based Design and Structure-Activity Relationship Studies, Zhichao Zhang et al., J. Med. Chem, 2011,54,1101-1105.
Probing the difference between BH3 groove of Mcl-1 and Bcl-2 protein: Implications for dual inhibitors design, Zhichao Zhang et al., E J. Med Chem, doi: 10.1016/j.ejmech2011.05.062 European. J. Med Chem (2011), 1-8 (Article in press).

* cited by examiner

*Primary Examiner* — Kahsay Habte
(74) *Attorney, Agent, or Firm* — Novick, Kim & Lee, PLLC; Allen Xue

(57) ABSTRACT

The present invention relates to acenaphtho heterocyclic compounds and their uses in manufacturing the BH3 mimetics as Bcl-2-like protein inhibitors. Structures are shown in the following:

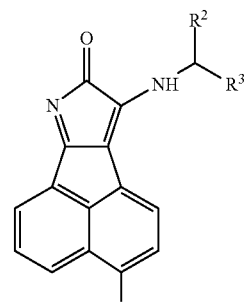

I

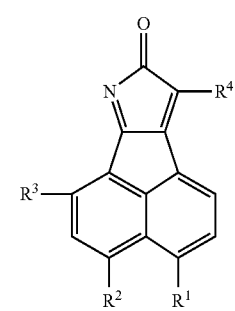

II

Statistical analysis of their bio-activities showed these compounds exhibit better BH3 mimicking property than the reported compounds. These compounds can simulate BH3-only protein, competitively bind and antagonizing Bcl-2 and Mcl-1 proteins in vitro and in cells, and then induce apoptosis. Therefore, they all can be used in the manufactures of anti-cancer compounds.

15 Claims, 3 Drawing Sheets

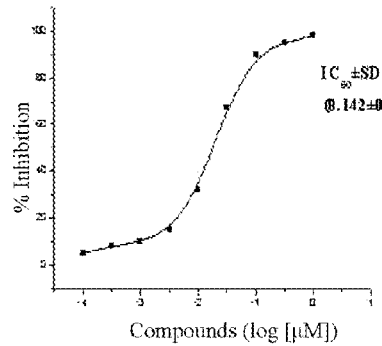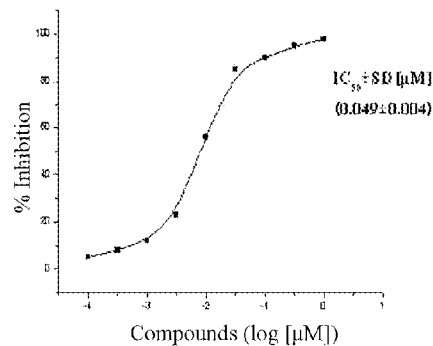
Figure 1      Figure 2
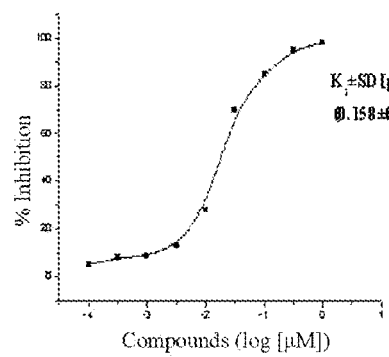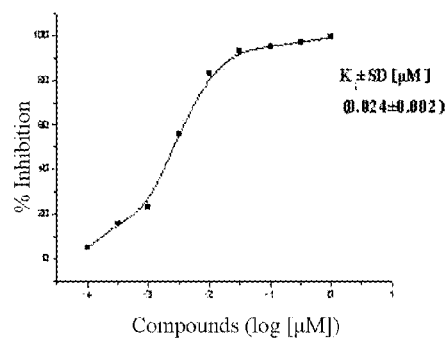
Figure 3      Figure 4
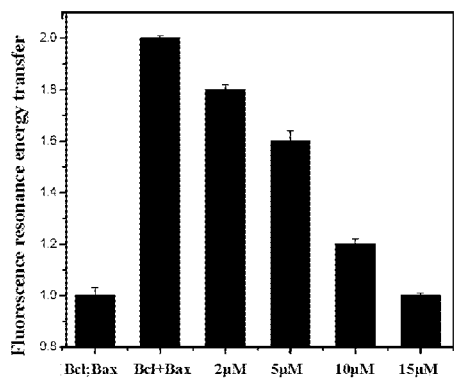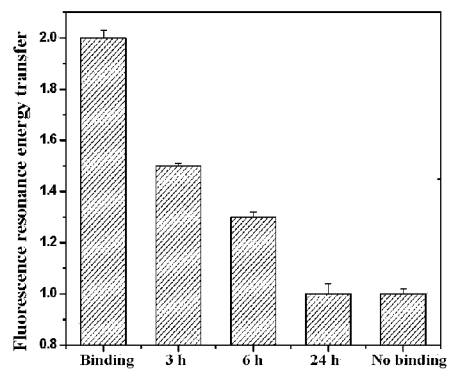
Figure 5      Figure 6

GFP-Bax　　Mitochondria specific probe　　Co-localization

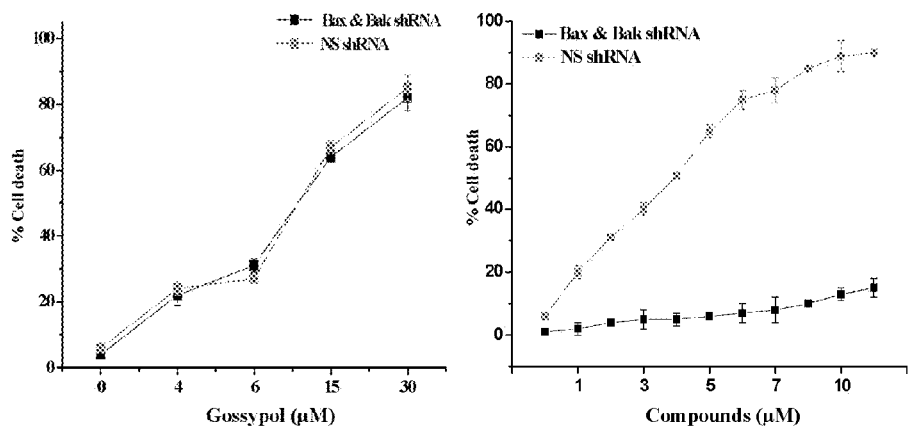
Figure 9
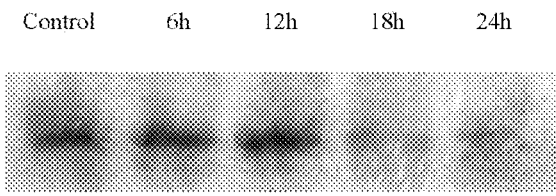
Figure 10
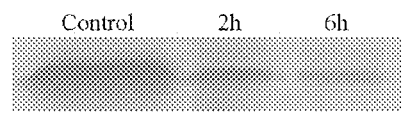
Figure 11
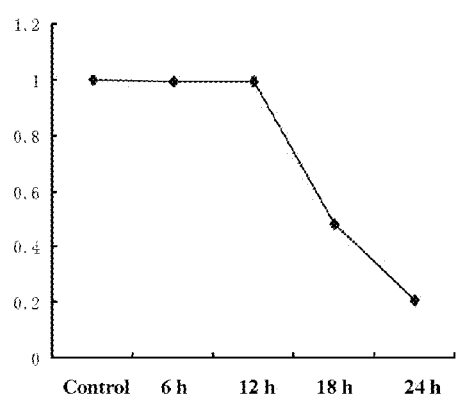 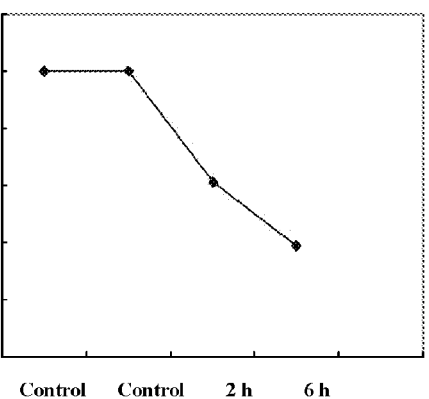
Figure 12          Figure 13

ACENAPHTHO HETEROCYCLIC COMPOUND AND APPLICATION THEREOF

TECHNICAL FIELD OF THE INVENTION

The invention relates to a new type of acenaphtho heterocyclic compounds identified as small molecule Bcl-2 inhibitors. These compounds can simulate BH3-only protein, competitively bind and antagonizie Bcl-2, Bcl-xL and Mcl-1 proteins in vitro and in vivo, to induce cell apoptosis. Therefore, they can be used as anticancer compounds.

BACKGROUND OF THE INVENTION

The molecule targeted antitumor drug is becoming a hot spot in new drug research and development and a new generation product during marketization after cytotoxic agents as antitumor drugs. Bcl-2 protein is the most important molecular target for antagonizing and reversing the immortality of malignant tumors. Therefore, specific antagonizing Bcl-2 protein will achieve the goals of anticancer therapy with high selectivity, safety, high performance and low painfulness by inducing intently apoptosis in tumor cells. Among Bcl-2 inhibitors, BH3 analogues (BH3 mimetics) with high selectivity exhibit the most remarkable antitumor effect, the best pharmacodynamic activity and the lowest toxic side effects. In addition, such inhibitors also must possess broad spectrum antagonizing ability on the anti-apoptotic members (including Bcl-2, Bcl-xL and Mcl-1 proteins) of the Bcl-2 family in order to gain single-agent efficacy and limited resistance.

However, until now, there are still no marketed antitumor products using Bcl-2 as target. Among the existing 19 preclinical Bcl-2 inhibitors, 3 optimal products are in phase I, phase II and phase III clinical trials respectively, they are ABT-737 researched and developed by Abbott Laboratories, Illinois, USA; Obatoclax (GX15-070) researched and developed by Gemin X; and AT-101 researched and developed by Ascenta in USA. They all are BH3 analogues. The competitive binding constant is up to grade nM with Bcl-2 protein, which is far higher than other 15 similar molecules. However, they all have the following deficiencies: the BH3 analogous level of Gossypol and Obatoclax is insufficient, they are not the authentic BH3 analogue, in other words, they possess cytotoxicity independent on BAX/BAK. This indicates that other target points exist, thus they have toxic side effects. Although ABT-737 is the authentic BH3 analogue, it cannot bind with Mcl-1 and cannot inhibit the Bcl-2 family proteins with broad spectrum, thereby severely limiting its application scope.

The present inventors disclosed a series of acenaphtho heterocyclic compounds of 8-oxo-8H-acenaphtho[1,2-b]pyrrole-9-carbonitrile, and disclosed that these compounds had the activity of inhibiting tumor growth through inducing cell apoptosis (Chinese patent, Authorized Announcement No. CN1304370C). However, as a potential antitumor drug on basis of apoptosis, its research and development faces the same difficulties as the similar drugs: the complexity of apoptosis signal gateway, the potential and intensive cytotoxicity as well as the inevitable blindness resulted from taking medicine. All of these are the important reasons for the failure in the development of such similar drugs. Therefore, the targeting effect of drugs should be prominently emphasized in the research course.

SUMMARY OF THE INVENTION

The present invention aims to provide compounds, which have stronger targeting and can be used as BH3 analogue, Bcl-2 family protein (including Bcl-2, Bcl-xL and Mcl-1 proteins) inhibitors.

One goal of the present invention is to provide acenaphtho heterocyclic compounds. They have the following structural formula:

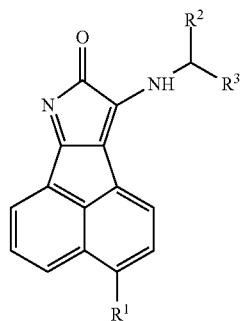

wherein:

$R^1$ is selected from H, thiomorpholinyl or $XR^4$;

$R^2$ is selected from $(CH_2)_nZ$ or $(CH_2)_nPh$-(o,m,p)Z; Z is selected from $NO_2$, Ph, $CF_3$, $OCH_3$, $SCH_3$, $NH_2$, $NHCH_3$, $N(CH_3)_2$, unsubstituted linear or branched $C_{1-8}$ alkyl and linear or branched $C_{1-8}$ alkyl that is substituted with halogen, amino, hydroxyl, ester or carboxyl;

$R^3$ is selected from $(CH_2)_nW$, W is selected from H, CN, $NO_2$, $NH_2$, COOH, CHO, OH or $SO_3H$;

$R^4$ is selected from $(CH_2)_nY$, thenoyl, tetrahydropyrane, tetrahydrothiapyran and $(CH_2)_nPh$-(o,m,p)Y; Y is selected from a straight or branched $C_{1-8}$ alkyl, wherein the straight or branched $C_{1-8}$ alkyl can be unsubstituted linear or substituted by halogen, amino, hydroxyl, ester or carboxyl;

X is selected from O, S, amino, carbonyl, ester, amide or sulfamide.

n is 0 to 4.

In the preferential technical proposal, Z is selected from a straight or branched $C_{1-4}$ alkyl, wherein the straight or branched $C_{1-4}$ alkyl can be unsubstituted or substituted.

In further preferential technical proposal, $R^2$ is selected from $(CH_2)_nPh$-(o,m,p)Z, wherein Z is selected from a straight or branched $C_{1-3}$ alkyl that can be unsubstituted or substituted.

In further preferential technical proposal, W is selected from H, $NH_2$ or OH.

In further preferential technical proposal, X is selected from O or S.

In further preferential technical proposal, $R^4$ is selected from Ph-$(CH_2)_nY$, wherein Y is selected from Ph, $CF_3$, $OCH_3$, $SCH_3$, $NH_2$, Br, isopropyl, isobutyl or secbutyl.

In certain embodiments, the compound of formula I is selected from:

9-(butylamino)-8H-acenaphtho[1,2-b]pyrrol-8-one;

9-(hexylamino)-8H-acenaphtho[1,2-b]pyrrol-8-one;

9-(3-phenylpropylamino)-8H-acenaphtho[1,2-b]pyrrol-8-one;

3-ethoxy-9-(3-phenylpropylamino)-8H-acenaphtho[1,2-b]pyrrol-8-one;

3-benzoyl-9-(butylamino)-8H-acenaphtho[1,2-b]pyrrol-8-one;

9-(butyl(methyl)amino)-8H-acenaphtho[1,2-b]pyrrol-8-one;

3-(4-bromophenylthio)-9-(butylamino)-8H-acenaphtho[1,2-b]pyrrol-8-one;

3-(4-bromophenylthio)-9-(3-phenylpropylamino)-8H-acenaphtho[1,2-b]pyrrol-8-one;

9-(butylamino)-3-thiomorpholino-8H-acenaphtho[1,2-b]pyrrol-8-one;

9-(3-phenylpropylamino)-3-thiomorpholino-8H-acenaphtho[1,2-b]pyrrol-8-one;

9-(butylamino)-3-(4-isopropylphenoxy)-8H-acenaphtho[1,2-b]pyrrol-8-one;

3-(4-isopropylphenoxy)-9-(3-phenylpropylamino)-8H-acenaphtho[1,2-b]pyrrol-8-one.

In another aspect of the invention, the general procedures used to synthesize the compounds of Formula I are described that the compounds of Formula i react with $NH_2CHR^2R^3$ under the room temperature for 0.5~8 h.

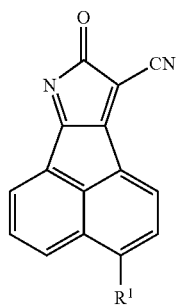

i

In the condensation, the optimum mole ration of compounds of Formula i to $NH_2CHR^2R^3$ is 1:5 and the solvent is acetonitrile.

wherein, the definition of the substituent is the consistent with the Formula I.

The general procedure used to synthesize the compounds of Formula I is a mild synthetic route. 8-oxo-8H-acenaphtho[1,2-b]pyrrole-9-carbonitrile and its derivatives react with $NH_2CHR^2R^3$ under the room temperature for 0.5-8 h. A series of amino-substituted acenaphtho heterocyclic compounds were obtained. As followed:

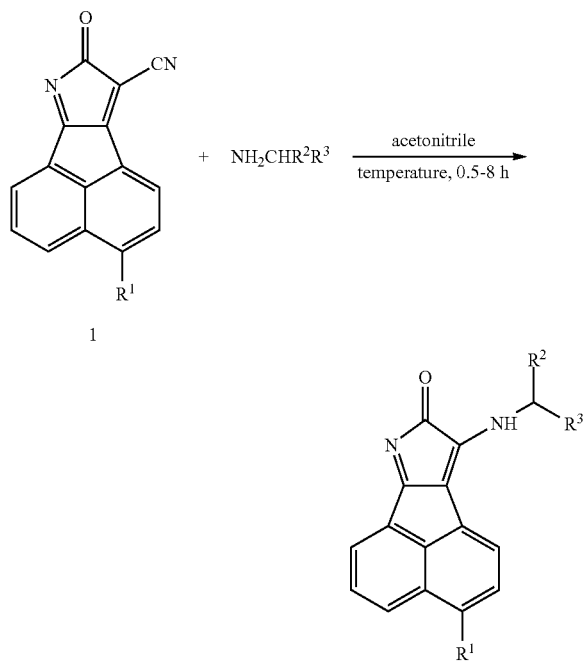

Based on the previous acenaphtho heterocyclic compounds, we obtain a series of new compounds of Formula I after the analysis and experiments. These compounds share common features, amino-substituted at 9-position. The statistical results demonstrated that these acenaphtho heterocyclic compounds enhance the inhibition capability against Bcl-2 and Mcl-1 proteins to some extent, can also be used to prepare the BH3 analogue, Bcl-2 family protein inhibitors, and further be used to prepare the antitumor drugs having high targeting.

In another aspect of the invention, the acenaphtho heterocyclic compounds of the present invention have the following structural Formula II:

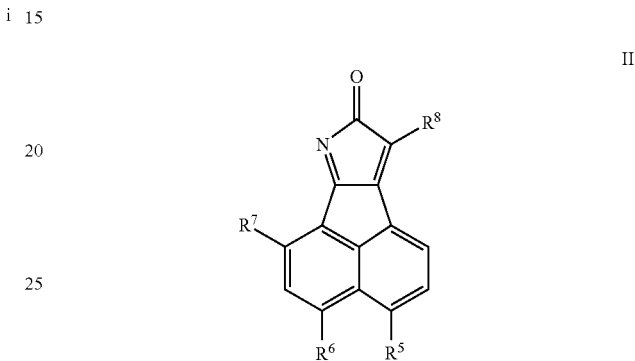

II wherein:
$R^5$, $R^6$ and $R^7$ are each independently selected from $XR^9$ or H;

$R^8$ is selected from CN, COOH, $COOR^{10}$ or $CONHR^{10}$;

X is selected from O, carbonyl, ester, amide or sulfamide;

where $R^9$ is selected from $(CH_2)_nY$ or $(CH_2)_nPh$-(o,m,p)Y; Y is selected from unsubstituted linear or branched $C_{2-8}$ alkyl and linear or branched $C_{1-8}$ alkyl that is substituted with halogen, amino, hydroxyl, ester or carboxyl;

where $R^{10}$ is selected from unsubstituted linear or branched $C_{1-6}$ alkyl that is substituted with halogen, amino, hydroxyl, ester, carboxyl or $(CH_2)_nPh$-(o,m,p)Z; Z is selected from $CH_3$, $C_2H_5$, $NO_2$, Ph, F, Cl, Br, $CF_3$, $OCH_3$, $SCH_3$, $NH_2$, $N(CH_3)_2$;

X is S;

where $R^9$ is selected from $(CH_2)_nPh$-(o,m,p)Y; Y is selected from linear or branched $C_{2-8}$ alkyl and linear or branched $C_{1-8}$ alkyl that is substituted with halogen, amino, hydroxyl, ester or carboxyl;

where $R^{10}$ is selected from unsubstituted linear or branched $C_{1-6}$ alkyl and linear or branched $C_{1-6}$ alkyl that is substituted with halogen, amino, hydroxyl, ester, carboxyl or $(CH_2)_nPh$-(o,m,p)Z; Z is selected from $CH_3$, $C_2H_5$, $NO_2$, Ph, F, Cl, Br, $CF_3$, $OCH_3$, $SCH_3$, $NH_2$, $N(CH_3)_2$;

n is 0 to 4.

In the preferential technical proposal, $R^5$ and $R^6$ are each independently selected from $XR^9$ or H.

In further preferential technical proposal, $R^8$ is CN.

In further preferential technical proposal, $R^9$ is selected from $(CH_2)_nPh$-(o,m,p)Y.

In further preferential technical proposal, X is selected from O or S; Y is selected from linear or branched $C_{3-5}$ alkyl.

In further preferential technical proposal, Y is selected from isopropyl, isobutyl or secbutyl.

In further preferential technical proposal, the compound of formula II is selected from:

3-(4-sec-butylphenoxy)-8-oxo-8H-acenaphtho[1,2-b]pyrrole-9-carbonitrile;

4-(4-sec-butylphenoxy)-8-oxo-8H-acenaphtho[1,2-b]pyrrole-9-carbonitrile;

3-(4-isobutylphenoxy)-8-oxo-8H-acenaphtho[1,2-b]pyrrole-9-carbonitrile;

4-(4-isobutylphenoxy)-8-oxo-8H-acenaphtho[1,2-b]pyrrole-9-carbonitrile;

3-(4-isopropylphenoxy)-8-oxo-8H-acenaphtho[1,2-b]pyrrole-9-carbonitrile;

3-(4-isobutylphenylthio)-8-oxo-8H-acenaphtho[1,2-b]pyrrole-9-carbonitrile;

4-(4-isobutylphenylthio)-8-oxo-8H-acenaphtho[1,2-b]pyrrole-9-carbonitrile;

3-(4-isopropylphenylthio)-8-oxo-8H-acenaphtho[1,2-b]pyrrole-9-carbonitrile;

3-(4-sec-butylphenylthio)-8-oxo-8H-acenaphtho[1,2-b]pyrrole-9-carbonitrile.

In another aspect of the invention, the compounds of the present invention can be synthesized by the following a or b routes:

a. In the first route, the raw material 8-oxo-8H-acenaphtho[1,2-b]pyrrole-9-carbonitrile having excellent rigid, coplanarity and strong electron deficiency undergoes aromatic hydrogenous nucleophilic substitution reaction with the nucleophilic reagents such as alcohol, thioalcohol, phenol or thiophenol, to obtain 3-, 6- or 3,6-substituted 8-oxo-8H-acenaphtho[1,2-b]pyrrole-9-carbonitrile. After the carbonitrile being hydrolyzed, esterified and amidated, the corresponding acid, ester and amide are obtained. The reaction formula is as follows:

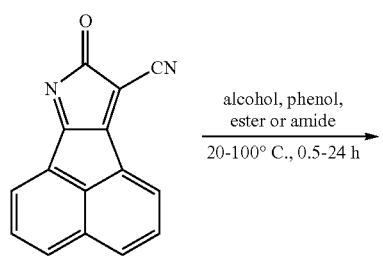

b. In the second route, the raw material acenaphthenequinone and the solvent concentrated sulfuric acid are added into liquid bromine and refluxed for 2 hours to obtain 5-bromoacenaphthylene-1,2-dione. The resulting bromoacenaphthene reacts with alcohol, thioalcohol, phenol, thiophenol, ester or amide to obtain the corresponding substituted acenaphthenequinone iv, as follows:

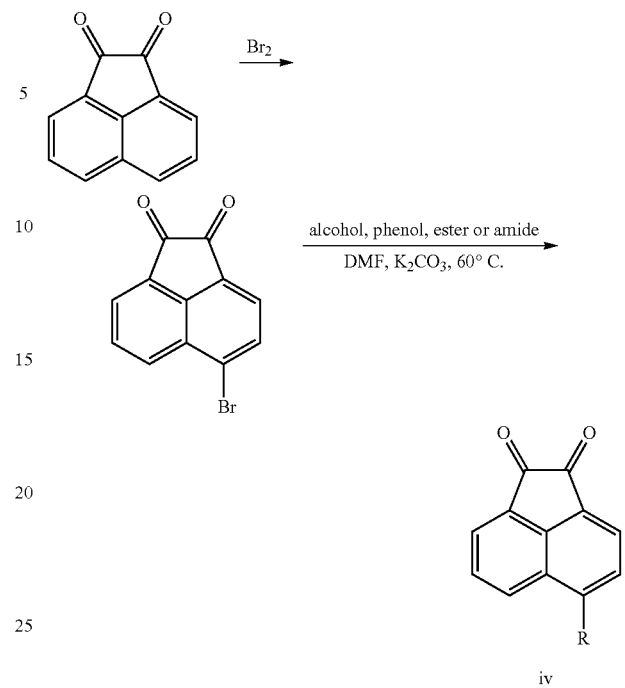

The resulting substituted acenaphthenequinone reacts with acetonitrile under the weak acid condition, such as gel silica, to obtain 3-(2-oxo-2H-acenaphthene)-malononitrile. After that, the reaction products are catalyzed by $K_2CO_3$ and refluxed with acetonitrile for 0.5-6 hours. Then cool and vaporize some solvent under decompression conditions. The corresponding 3- or 4-monosubstituted oxy-8-oxo-8H-acenaphtho[1,2-b]pyrrole-9-carbonitrile (ii or iii) is obtained by filtering or direct column chromatography. After the carbonitrile being hydrolyzed, esterified and amidated, the corresponding acid, ester and amide are obtained.

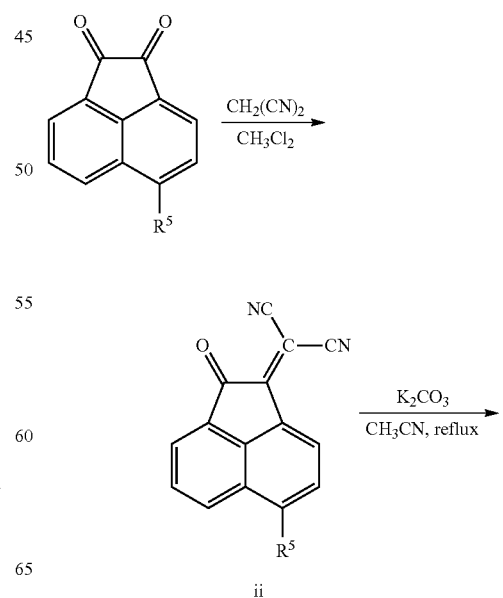

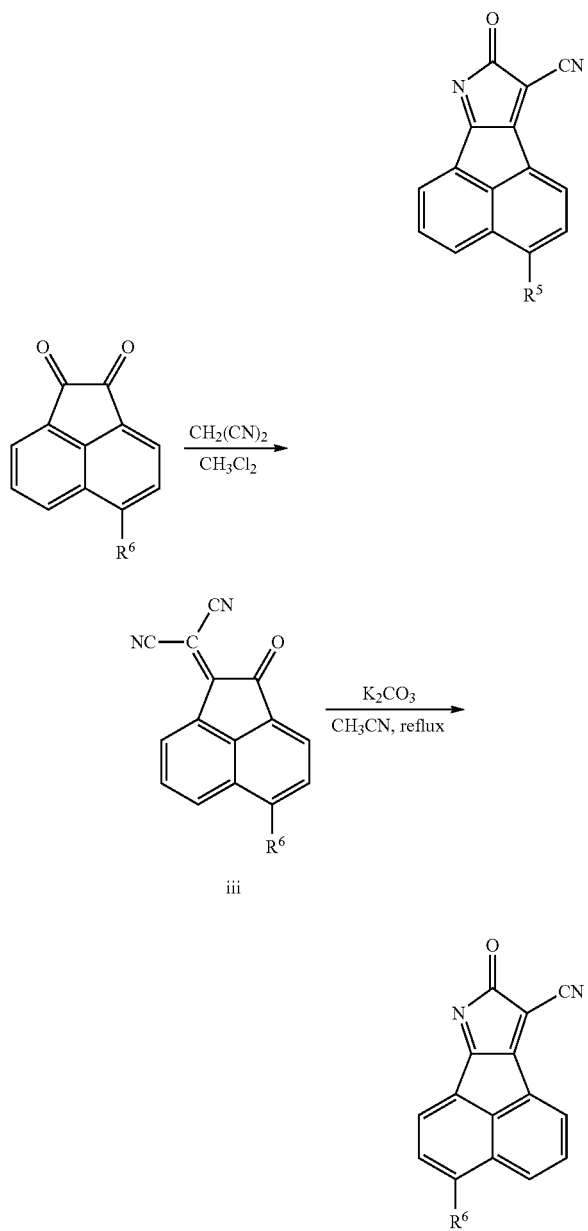

iii

Wherein, the definition of the substituent is the consistent with the Formula II. The substituent group R in different replace sites is distinguished into R5 or R6.

Based on previously discovered acenaphtho heterocyclic compounds, the present invention screened for a series of new compounds with structural formula II by means of various analysis and experiments. The results demonstrated that the acenaphtho heterocyclic compounds in present invention have similar or more excellent BH3 analogous level than that have been published. They can also be used to prepare the BH3 analogue, Bcl-2 family protein inhibitors.

Therefore, one objective of the present invention is to provide the uses of the above-mentioned acenaphtho heterocyclic compounds in manufacturing the BH3 analogue, Bcl-2 family protein inhibitors. It also includes formulation procedures of compounds with structural formula I and II, and the composition comprises an effective dose of the acenaphtho heterocyclic compounds and a moderate amount of pharmaceutical adjuvant. According to the test results in the examples, the effective dose of compounds needed to fulfill the uses in the present invention might be lower than those have been previously published. Furthermore, another objective of the present invention is to provide the uses of the above-mentioned acenaphtho heterocyclic compounds in manufacturing antitumor drugs having high targeting.

BRIEF DESCRIPTION OF DRAWINGS

There are 13 drawings in the present invention, wherein:

FIG. 1 is the dynamic curve of the compound 1 and FAM-Bid peptide competitively binding Bcl-2 protein detected by the ELISA method;

FIG. 2 is the dynamic curve of the compound 1 and FAM-Bid peptide competitively binding Mcl-1 protein detected by the ELISA method;

FIG. 3 is the dynamic curve of the compound 13 and FAM-Bid peptide competitively binding Bcl-2 protein detected by the fluorescence polarization method;

FIG. 4 is the dynamic curve of the compound 13 and FAM-Bid peptide competitively binding Mcl-1 protein detected by the fluorescence polarization method;

FIG. 5 shows the interactions between Bcl-2 and Bax on a cellular level interfered by the compound 1 (different concentration);

FIG. 6 shows the interactions between Bcl-2 and Bax on a cellular level interfered by the compound 1 (different action time);

FIG. 9 shows the results of the cell toxicity of the compound 1 depending on BAX/BAK (Gossypol is nonspecific comparison);

FIG. 10 is the western blotting electropherogram showing the inhibition of the compound 1 against Mcl-1;

FIG. 11 is the western blotting electropherogram showing the inhibition of the compound 1 against Bcl-2;

FIG. 12 is the semiquantitative curve showing the inhibition of the compound 1 against Mcl-1 protein;

FIG. 13 is the semiquantitative curve showing the inhibition of the compound 1 against Bcl-2 protein;

DETAILED DESCRIPTION OF PREFERRED EMBODIMENTS

Figure 7:
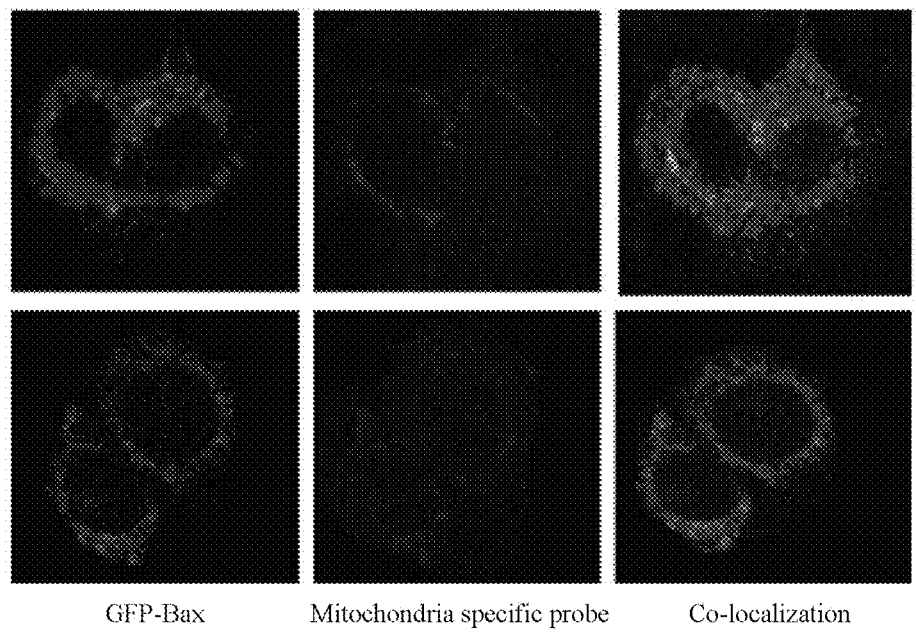
FIG. 7 shows the positive results of BH3 analogous degree of the compound 1 detected by Bax protein and mitochondria co-localization.

Various embodiments of the present invention will now be described more fully with reference to the accompanying drawings.

Part I: Preparation and Characterization of Compounds Against Bcl-2 Family Proteins

EXAMPLE 1

Synthesis and Characterization of 9-n-Butylamino-8H-acenaphtho[1,2-b)]pyrrol-8-one (1)

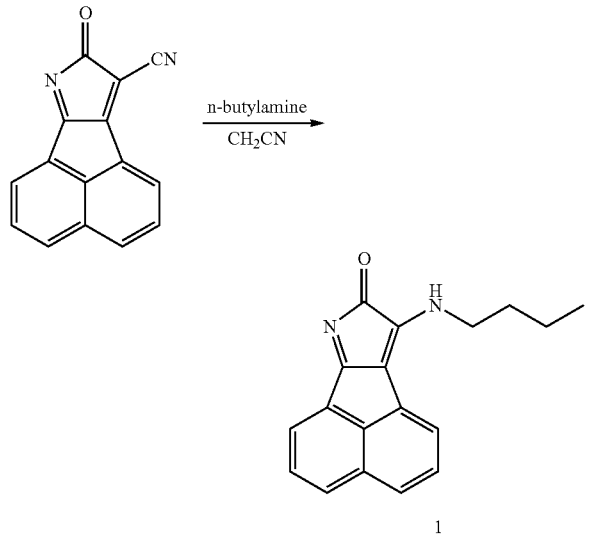

0.23 g 8-oxo-8H-acenaphtho[1,2-b]pyrrole-9-carbonitrile and 0.49 mL n-butylamine were dissolved in acetonitrile (50 ml), and then stirred at room temperature for 1 h. The solvent was reduced in vacuo and the residue was purified by normal phase column chromatography on silica gel with a yield of 22%.

Characterization of 9-n-Butylamino-8H-acenaphtho[1,2-b]pyrrol-8-one (1): M.p. 232-233° C. $^1$H NMR (400M, CDCl$_3$): δ 8.63 (d, J=8.0 Hz, 1H), 8.16 (d, J=8.0 Hz, 1H), 8.13 (d, J=8.4 Hz, 1H), 7.95 (d, J=8.0 Hz, 1H), 7.75 (t, J=8.0 Hz, 1H), 7.67 (t, J=8.0 Hz, 1H), 4.08 (m, 2H), 2.71 (br, 1H), 1.85 (m, 2H), 1.55 (m, 2H), 0.98 (t, J=8.0 Hz, 3H). TOF MS (EI$^+$): C$_{18}$H$_{16}$N$_2$O, (m/z): calcd for 276.1263, found 276.1266.

EXAMPLE 2

Synthesis and Characterization of 9-n-Hexylamino-acenaphtho[1,2-b]pyrrol-8-one (2)

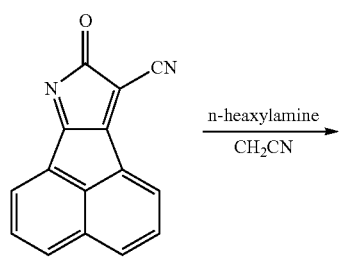

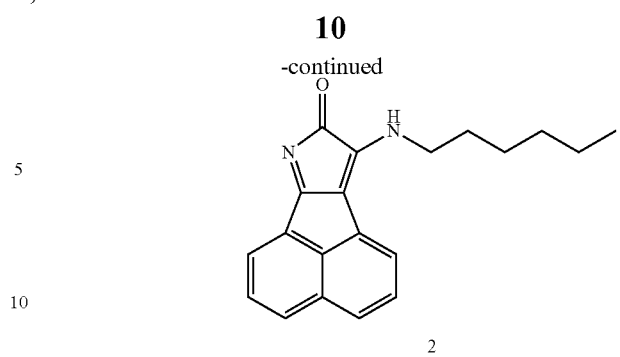

0.23 g 8-oxo-8H-acenaphtho[1,2-b]pyrrole-9-carbonitrile and 0.51 mL n-Hexylamine were dissolved in acetonitrile (50 ml), and then stirred at room temperature for 1 h. The solvent was reduced in vacuo and the residue was purified by normal phase column chromatography on silica gel with a yield of 25%.

Characterization of 9-n-Hexylamino-acenaphtho[1,2-b]pyrrol-8-one (2): M.p. 234-235° C. $^1$H NMR (400 M, CDCl$_3$): δ 8.65 (d, J=8.0 Hz, 1H), 8.10 (d, J=8.0 Hz, 1H), 8.05 (d, J=8.4 Hz, 1H), 7.98 (d, J=8.0 Hz, 1H), 7.63 (t, J=8.0 Hz, 1H), 7.47 (t, J=8.0 Hz, 1H), 4.09 (m, 2H), 3.69 (br, 1H), 1.84 (m, 2H), 1.55-1.25 (m, 6H), 0.95 (t, J=8.0 Hz, 3H). TOF MS (EI$^+$): C$_{20}$H$_{20}$N$_2$O, (m/z): calcd for 304.1576, found 304.1579.

EXAMPLE 3

Synthesis and Characterization of 9-(3-Phenyl-propylamino)-acenaphtho[1,2-b]pyrrol-8-one (3)

0.23 g 8-oxo-8H-acenaphtho[1,2-b]pyrrole-9-carbonitrile and 0.77 mL 3-phenylpropan-1-amine were dissolved in acetonitrile (50 ml), and then stirred at room temperature for 2 h. The solvent was reduced in vacuo and the residue was purified by normal phase column chromatography on silica gel with a yield of 20%.

Characterization of 9-(3-Phenyl-propylamino)-acenaphtho[1,2-b]pyrrol-8-one (3): M.p. 252-253° C. $^1$H NMR (400 M, CDCl$_3$): δ 8.61 (d, J=8.0 Hz, 1H), 8.09 (d, J=8.0 Hz, 2H), 7.73 (t, J=8.0 Hz, 2H), 7.54 (t, J=8.0 Hz, 1H), 7.47 (d, J=8.0

Hz, 1H), 7.34 (m, 3H), 7.16 (d, J=8.0 Hz, 1H), 5.9 (br, 1H), 4.09 (m, 2H), 1.84 (m, 2H), 1.25 (m, 2H). TOF MS (EI+): $C_{23}H_{18}N_2O$, (m/z): calcd for 338.1419, found 338.1415.

EXAMPLE 4

Synthesis and Characterization of 3-Ethoxy-9-(3-phenyl-propylamino)-acenaphtho[1,2-b]pyrrol-8-one (4)

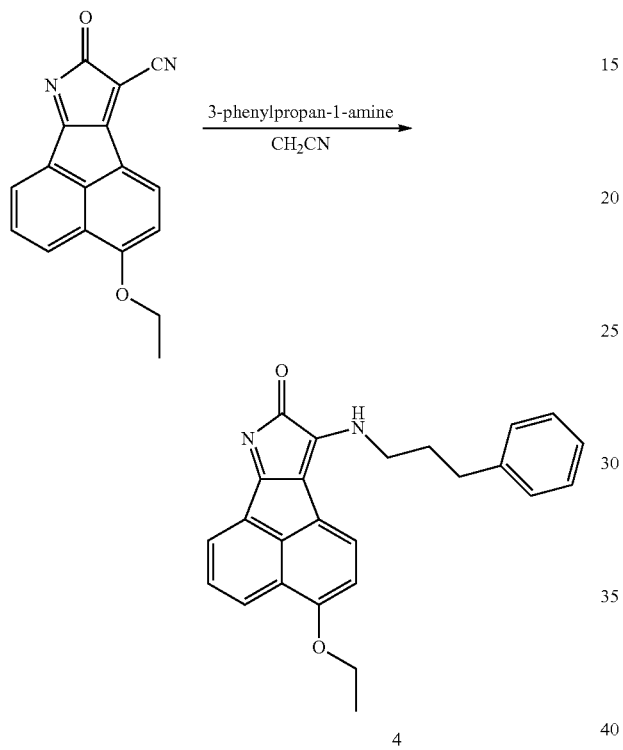

0.27 g 3-Ethoxy-8-oxo-8H-acenaphtho[1,2-b]pyrrole-9-carbonitrile and 0.77 mL 3-phenylpropan-1-amine were dissolved in acetonitrile (50 ml), and then stirred at room temperature for 2 h. The solvent was reduced in vacuo and the residue was purified by normal phase column chromatography on silica gel with a yield of 20%.

Characterization of 3-Ethoxy-9-(3-phenyl-propylamino)-acenaphtho[1,2-b]pyrrol-8-one (4): M.p. 250-251° C. $^1$H NMR (400M, CDCl$_3$): δ 8.55 (d, J=8.0 Hz, 1H), 8.42 (d, J=8.0 Hz, 1H), 7.82 (t, J=8.4 Hz, 1H), 7.79 (d, J=8.0 Hz, 1H), 7.41 (t, J=8.4 Hz, 2H), 7.30 (d, J=8.4 Hz, 2H), 7.12 (t, J=8.4 Hz, 1H), 6.60 (d, J=8.4 Hz, 1H), 4.62 (q, J=7.6 Hz, 2H), 2.87 (t, J=8.4 Hz, 2H), 2.62 (t, J=8.4 Hz, 2H), 2.09 (m, J=8.4 Hz, 2H), 2.01 (br, 1H), 1.31 (t, J=7.6 Hz, 3H). TOF MS EI+: $C_{24}H_{20}N_2O_2$, (m/z): calcd for 382.1681, found 382.1683.

EXAMPLE 5

Synthesis and Characterization of 3-Benzoyl-9-butylamino-acenaphtho[1,2-b]pyrrol-8-one (5)

0.33 g 3-Benzoyl-8-oxo-8H-acenaphtho[1,2-b]pyrrole-9-carbonitrile and 0.47 mL n-butylamine were dissolved in acetonitrile (50 ml), and then stirred at room temperature for 2 h. The solvent was reduced in vacuo and the residue was purified by normal phase column chromatography on silica gel with a yield of 20%.

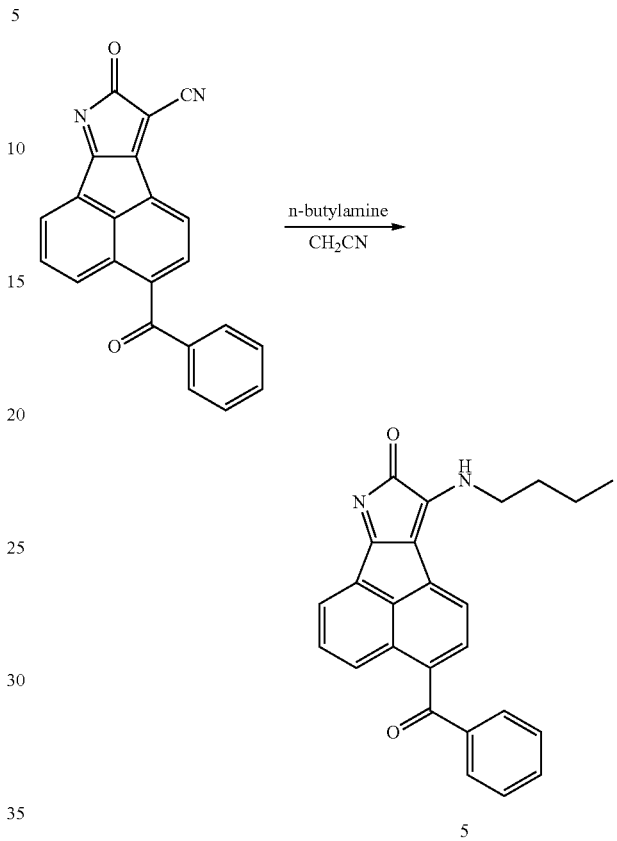

Characterization of 3-Benzoyl-9-butylamino-acenaphtho[1,2-b]pyrrol-8-one (5): M.p. 262-263° C. $^1$H NMR (400M, CDCl$_3$): δ 8.96 (d, J=8.0 Hz, 1H), 8.56 (d, J=8.0 Hz, 1H), 8.15 (d, J=8.4 Hz, 1H), 8.01 (t, J=8.0 Hz, 1H), 7.81 (d, J=8.4 Hz, 1H), 7.80 (d, J=8.4 Hz, 2H), 7.68 (t, J=8.4 Hz, 1H), 7.48 (t, J=8.4 Hz, 2H), 3.87 (t, J=8.4 Hz, 2H), 2.01 (br, 1H), 1.62 (m, 1.30 (m, 2H), 0.91 (t, J=7.6 Hz, 3H). TOF MS EI+: $C_{24}H_{20}N_2O_2$, (m/z): calcd for 380.1525, found 380.1523.

EXAMPLE 6

Synthesis and Characterization of 9-(Butyl-methyl-amino)-acenaphtho[1,2-b]pyrrol-8-one (6)

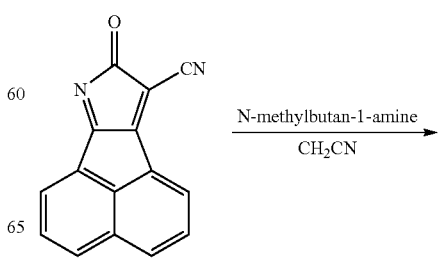

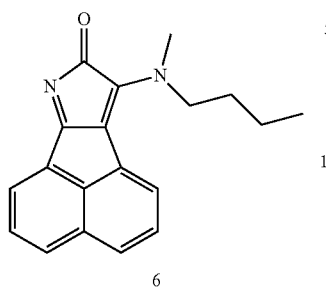

6

0.23 g 8-oxo-8H-acenaphtho[1,2-b]pyrrole-9-carbonitrile and 0.51 mL N-methylbutan-1-amine were dissolved in acetonitrile (50 ml), and then stirred at room temperature for 1 h. The solvent was reduced in vacuo and the residue was purified by normal phase column chromatography on silica gel with a yield of 25%.

Characterization of 9-(Butyl-methyl-amino)-acenaphtho[1,2-b]pyrrol-8-one (6): M.p. 245-246° C. $^1$H NMR (400M, CDCl$_3$): δ 8.45 (d, J=8.0 Hz, 1H), 8.30 (d, J=8.0 Hz, 1H), 8.05 (d, J=8.4 Hz, 1H), 7.98 (t, J=8.0 Hz, 1H), 7.87 (d, J=8.0 Hz, 1H), 7.63 (t, J=8.0 Hz, 1H), 3.09 (s, 3H), 2.55 (t, J=8.0 Hz, 2H), 1.39 (m, 2H), 1.29 (m, 2H), 0.95 (t, J=8.0 Hz, 3H). TOF MS (EI$^+$): C$_{19}$H$_{18}$N$_2$O, (m/z): calcd for 290.1419, found 290.1415.

EXAMPLE 7

Synthesis and Characterization of 3-(4-Bromo-phenylsulfanyl)-9-butylamino-acenaphtho[1,2-b]pyrrol-8-one (7)

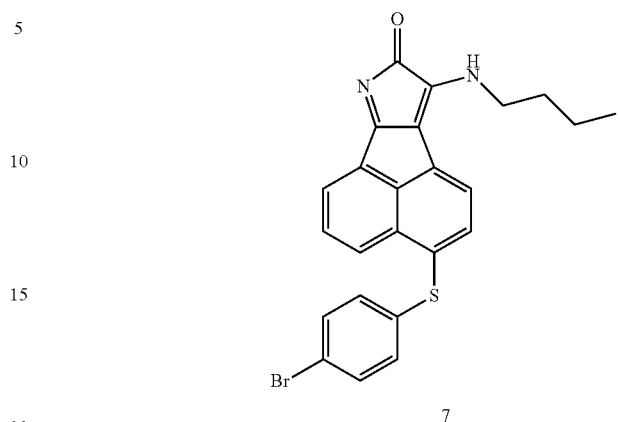

7

0.42 g 3-(4-Bromo-phenylsulfanyl)-8-oxo-8H-acenaphtho[1,2-b]pyrrole-9-carbonitrile and 0.47 mL n-butylamine were dissolved in acetonitrile (50 ml), and then stirred at room temperature for 2 h. The solvent was reduced in vacuo and the residue was purified by normal phase column chromatography on silica gel with a yield of 23%.

Characterization of 3-(4-Bromo-phenylsulfanyl)-9-butylamino-acenaphtho[1,2-b]pyrrol-8-one (7): M.p. 245-246° C. $^1$H NMR (400M, CDCl$_3$): δ 8.74 (br, 1H), 8.57 (d, J=8.0 Hz, 1H), 8.47 (d, J=8.0 Hz, 1H), 8.44 (d, J=8.0 Hz, 1H), 7.88 (t, J=8.0 Hz, 1H), 7.63 (d, J=8.0 Hz, 2H), 7.56 (d, J=8.0 Hz, 1H), 7.38 (d, J=8.0 Hz, 2H), 3.89 (m, 2H), 1.75 (m, 2H), 1.41 (m, 2H), 0.94 (t, J=8.0 Hz, 3H). TOF MS (EI$^+$): C$_{24}$H$_{19}$BrN$_2$OS, (m/z): calcd for 462.0401, found 462.0405.

EXAMPLE 8

Synthesis and Characterization of 3-(4-Bromo-phenylsulfanyl)-9-(3-phenyl-propylamino)-acenaphtho[1,2-b]pyrrol-8-one (8)

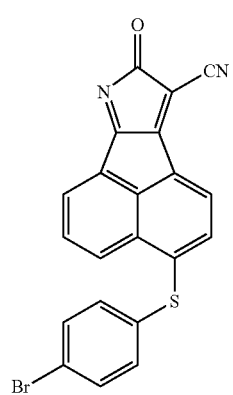 → n-butylamine / CH$_2$CN → 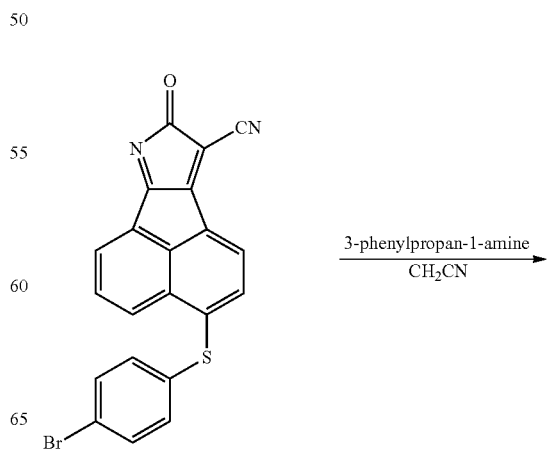 → 3-phenylpropan-1-amine / CH$_2$CN →

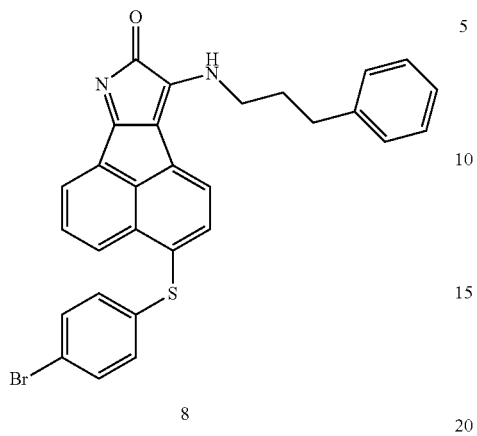

8

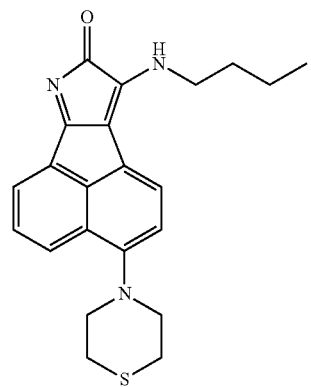

9

0.42 g 3-(4-Bromo-phenylsulfanyl)-8-oxo-8H-acenaphtho[1,2-b]pyrrole-9-carbonitrile and 0.77 mL 3-phenylpropan-1-amine were dissolved in acetonitrile (50 ml), and then stirred at room temperature for 2 h. The solvent was reduced in vacuo and the residue was purified by normal phase column chromatography on silica gel with a yield of 19%.

Characterization of 3-(4-Bromo-phenylsulfanyl)-9-(3-phenyl-propylamino)-acenaphtho[1,2-b]pyrrol-8-one (8): M.p. 272-273° C. $^1$H NMR (400 M, CDCl$_3$): δ 8.57 (d, J=8.0 Hz, 1H), 8.47 (d, J=8.0 Hz, 1H), 8.44 (d, J=8.0 Hz, 1H), 7.88 (t, J=8.0 Hz, 1H), 7.63 (m, 4H), 7.56 (d, J=8.0 Hz, 1H), 7.47 (m, 3H), 7.38 (d, J=8.0 Hz, 2H), δ 6.74 (br, 1H), 3.89 (m, 2H), 1.75 (m, 2H), 1.41 (m, 2H). TOF MS (EI$^+$): C$_{29}$H$_{21}$BrN$_2$OS, (m/z): calcd for 524.0588, found 524.0585.

0.33 g 8-Oxo-3-thiomorpholin-4-yl-8H-acenaphtho[1,2-b]pyrrole-9-carbonitrile and 0.47 mL n-butylamine were dissolved in acetonitrile (50 ml), and then stirred at room temperature for 2.5 h. The solvent was reduced in vacuo and the residue was purified by normal phase column chromatography on silica gel with a yield of 25%.

Characterization of 9-Butylamino-3-thiomorpholin-4-yl-acenaphtho[1,2-b]pyrrol-8-one (9): M.p. 239-240° C. $^1$H NMR (400 M, CDCl$_3$): δ 8.59 (d, J=8.0 Hz, 1H), 8.32 (d, J=8.0 Hz, 1H), 8.00 (d, J=8.4 Hz, 1H), 7.68 (t, J=8.0 Hz, 1H), 7.16 (d, J=8.4 Hz, 1H), 6.35 (br, 1H), 4.01 (m, —NHCH$_2$CH$_2$—, 2H), 3.51 (br s, —N(CH$_2$CH$_2$)$_2$S), 2.97 (br s, —N(CH$_2$CH$_2$)$_2$S), 1.84 (m, —NH CH$_2$CH$_2$CH$_2$—, 2H), 1.50 (m, —CH$_2$CH$_2$CH$_2$CH$_2$, 2H), 0.95 (t, J=8.0 Hz, 3H). TOF MS (EI$^+$): C$_{22}$H$_{23}$N$_3$OS, (m/z): calcd for 377.1562, found 377.1565.

EXAMPLE 9

Synthesis and Characterization of 9-Butylamino-3-thiomorpholin-4-yl-acenaphtho[1,2-b]pyrrol-8-one (9)

EXAMPLE 10

Synthesis and Characterization of 9-(3-Phenyl-propylamino)-3-thiomorpholin-4-yl-acenaphtho[1,2-b]pyrrol-8-one (10)

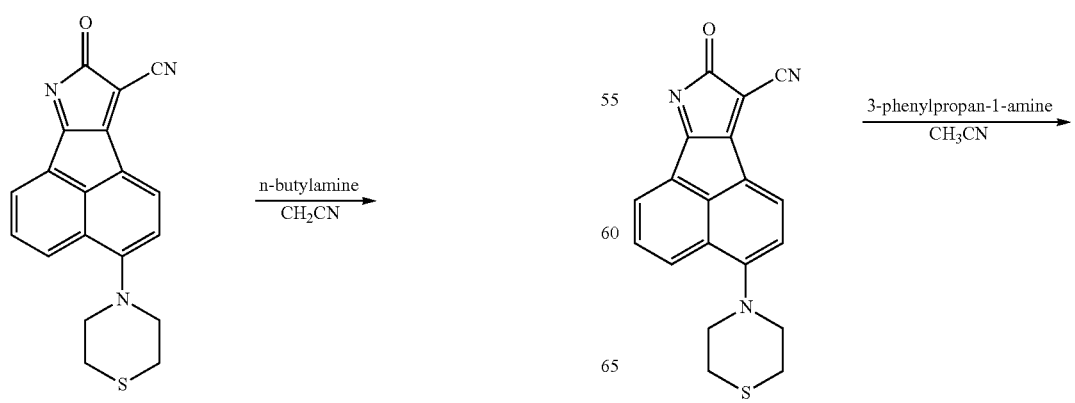

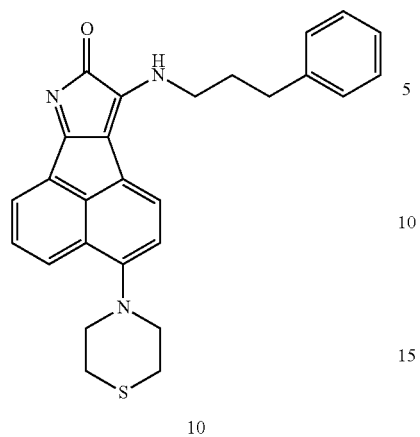

10

0.33 g 8-Oxo-3-thiomorpholin-4-yl-8H-acenaphtho[1,2-b]pyrrole-9-carbonitrile and 0.47 mL 3-phenylpropan-1-amine were dissolved in acetonitrile (50 ml), and then stirred at room temperature for 2.5 h. The solvent was reduced in vacuo and the residue was purified by normal phase column chromatography on silica gel with a yield of 18%.

Characterization of 9-(3-Phenyl-propylamino)-3-thiomorpholin-4-yl-acenaphtho[1,2-b]pyrrol-8-one (10): M.p. 265-266° C. $^1$H NMR (400 M, CDCl$_3$): δ 8.58 (d, J=8.0 Hz, 1H), 8.34 (d, J=8.0 Hz, 1H), 8.08 (d, J=8.4 Hz, 1H), 7.68 (m, 4H), 7.16 (m, 3H), 5.05 (br, 1H), 4.00 (m, 2H), 3.52 (br s, —N(CH$_2$CH$_2$)$_2$S), 2.89 (br s, —N(CH$_2$CH$_2$)$_2$S), 1.85 (m, 2H), 1.56 (m, 2H). TOF MS (EI$^+$): C$_{27}$H$_{25}$N$_3$OS, (m/z): calcd for 439.1718, found 439.1715.

EXAMPLE 11

Synthesis and Characterization of 9-Butylamino-3-(4-isopropyl-phenoxy)-acenaphtho[1,2-b]pyrrol-8-one (11)

11

0.36 g 3-(4-Isopropyl-phenoxy)-8-oxo-8H-acenaphtho[1,2-b]pyrrole-9-carbonitrile and 0.47 mL n-butylamine were dissolved in acetonitrile (50 ml), and then stirred at room temperature for 3 h. The solvent was reduced in vacuo and the residue was purified by normal phase column chromatography on silica gel with a yield of 23%.

Characterization of 9-Butylamino-3-(4-isopropyl-phenoxy)-acenaphtho[1,2-b]pyrrol-8-one (11): M.p. 243-244° C. $^1$H NMR (400 M, CDCl$_3$): δ 8.69 (d, J=8.0 Hz, 1H), 8.47 (d, J=8.0 Hz, 1H), 8.08 (d, J=8.0 Hz, 1H), 7.69 (t, J=8.0 Hz, 1H), 7.32 (d, J=8.0 Hz, 2H), 7.09 (d, J=8.0 Hz, 1H), 6.90 (d, J=8.0 Hz, 2H), 6.13 (br, 1H), 4.08 (m, 2H), 2.97 (m, 1H), 1.85 (m, 2H), 1.55 (m, 2H), 1.02 (s, 6H), 0.88 (t, J=8.0 Hz, 3H). TOF MS (EI$^+$): C$_{27}$H$_{26}$N$_2$O$_2$, (m/z): calcd for 410.1994, found 410.1998.

EXAMPLE 12

Synthesis and Characterization of 3-(4-Isopropyl-phenoxy)-9-(3-phenyl-propylamino)-acenaphtho[1,2-b]pyrrol-8-one (12)

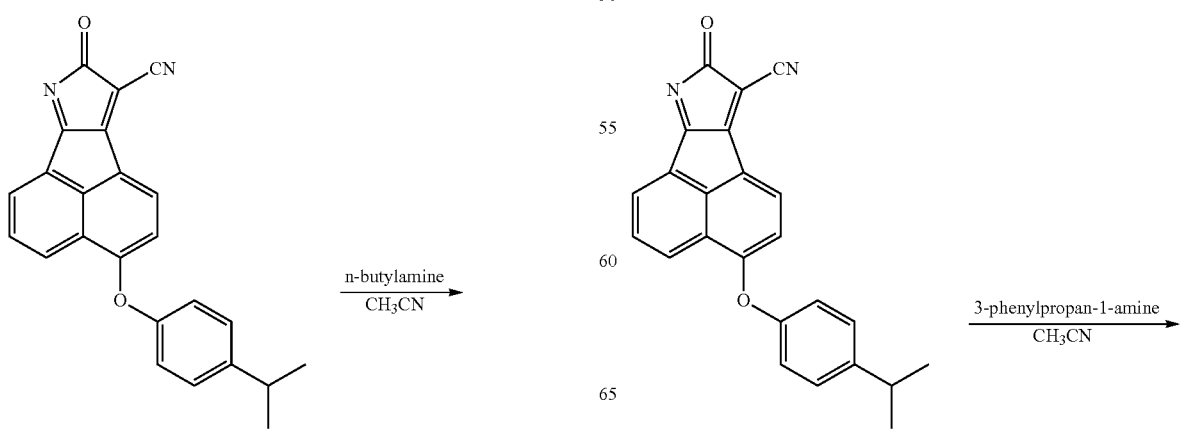

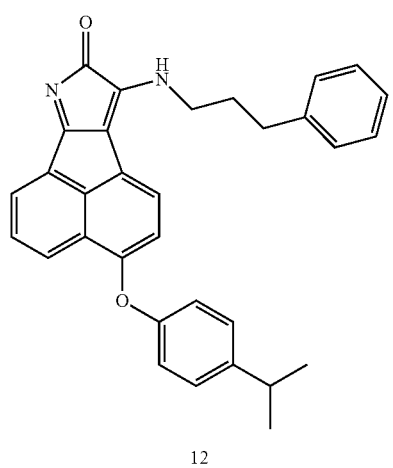

12

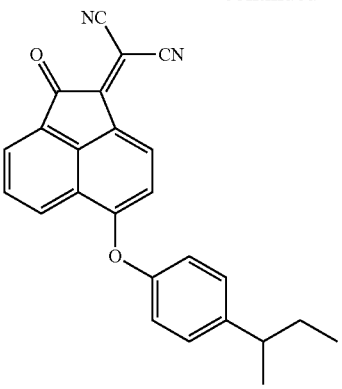

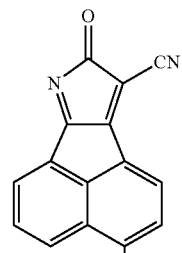

13

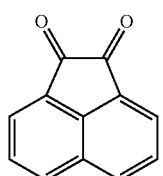

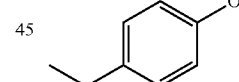

0.36 g 3-(4-Isopropyl-phenoxy)-8-oxo-8H-acenaphtho[1,2-b]pyrrole-9-carbonitrile and 0.77 mL 3-phenylpropan-1-amine were dissolved in acetonitrile (50 ml), and then stirred at room temperature for 3 h. The solvent was reduced in vacuo and the residue was purified by normal phase column chromatography on silica gel with a yield of 19%.

Characterization of 3-(4-Isopropyl-phenoxy)-9-(3-phenyl-propylamino)-acenaphtho[1,2-b]pyrrol-8-one (12): M.p. 275-276° C. $^1$H NMR (400 M, CDCl$_3$): δ 8.59 (d, J=8.0 Hz, 1H), 8.46 (d, J=8.0 Hz, 1H), 7.98 (t, J=8.0 Hz, 1H), 7.65 (d, J=8.0 Hz, 1H), 7.46 (d, J=8.0 Hz, 2H), 7.39 (t, J=8.0 Hz, 2H), 7.31-7.26 (m, 5H), 6.80 (d, J=8.0 Hz, 1H), 5.13 (br, 1H), 3.88 (m, 2H), 2.95 (m, 1H), 1.75 (m, 2H), 1.41 (m, 2H). 1.85 (m, 2H), 1.55 (m, 2H), 1.02 (s, 6H), TOF MS (EI$^+$): C$_{32}$H$_{28}$N$_2$O$_2$, (m/z): calcd for 472.2151, found 472.2156.

EXAMPLE 13

Synthesis and Characterization of 3-(4-sec-Butyl-phenoxy)-8-oxo-8H-acenaphtho[1,2-b]pyrrole-9-carbonitrile (13) and 4-(4-sec-Butyl-benzyl)-8-oxo-8H-acenaphtho[1,2-b]pyrrole-9-carbonitrile (14)

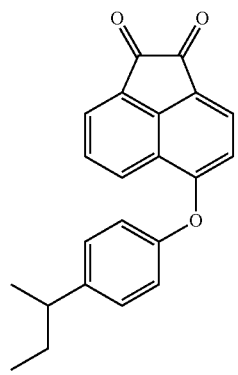

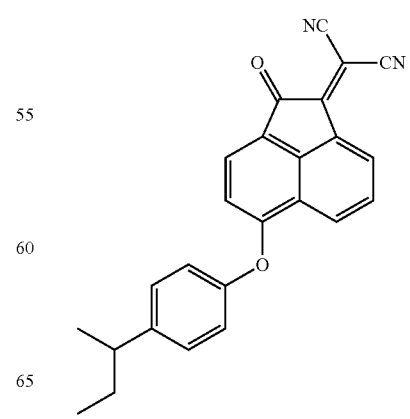

-continued

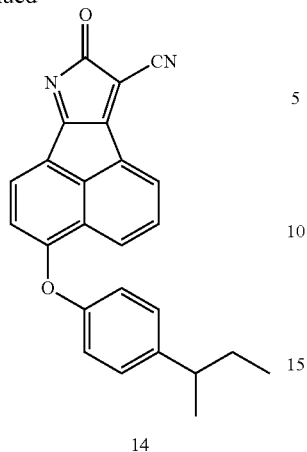

14

0.99 g 5-(4-sec-Butyl-phenoxy)-acenaphthylene-1,2-dione and 0.33 g malononitrile were dissolved in dichloromethane, and then mixture was applied to a gel silica column and eluted quickly. After all the mixture passed through, the column was spun dry. Red solid was obtained with a weight of 1.07 g and a yield of 94%. 0.05 g of $K_2CO_3$ and 20 mL of acetonitrile were added into 0.77 g of the red solid. The mixture was heated and refluxed for 3 hours. After the reaction finished, the reaction solution was spun dry and separated by chromatographic column ($CH_2Cl_2$: petroleum ether=1:1) to obtain two isomers.

Characterization of 13: M.p. 219-220° C. $^1$H NMR (400M, $CDCl_3$): δ 8.92 (d, J=8.0 Hz, 1H), 8.65 (d, J=8.8 Hz, 1H), 8.46 (d, J=8.0 Hz, 1H), 7.87 (t, J=8.0 Hz, 1H), 7.33 (d, J=8.4 Hz, 2H), 7.14 (d, J=8.4 Hz, 2H), 7.04 (d, J=8.0 Hz, 1H), 2.70 (m, 1H), 1.65 (m, 2H), 1.30 (d, J=8.0 Hz, 3H), 0.88 (t, J=8.0 Hz, 3H). TOF MS (EI$^+$): $C_{25}H_{18}N_2O_2$, (m/z): calcd for 378.1368, found 378.1376.

Characterization of 14: M.p. 278-279° C. $^1$H NMR (400M, $CDCl_3$): δ 8.76 (d, J=7.6 Hz, 1H), 8.60 (d, J=8.0 Hz, 1H), 8.42 (d, J=7.6 Hz, 1H), 7.88 (t, J=8.0 Hz, 1H), 7.40 (d, J=8.0 Hz, 2H), 7.09 (d, J=8.0 Hz, 2H), 6.95 (d, J=8.0 Hz, 1H), 2.70 (m, 1H), 1.65 (m, 2H), 1.30 (d, J=8.0 Hz, 3H), 0.88 (t, J=8.0 Hz, 3H). TOF MS EI$^+$: $C_{25}H_{18}N_2O_2$, (m/z): calcd for 378.1368, found 378.1362.

EXAMPLE 14

Synthesis and Characterization of 3-(4-Isobutyl-phenoxy)-8-oxo-8H-acenaphtho[1,2-b]pyrrole-9-carbonitrile (15) and 4-(4-Isobutyl-phenoxy)-8-oxo-8H-acenaphtho[1,2-b]pyrrole-9-carbonitrile (16)

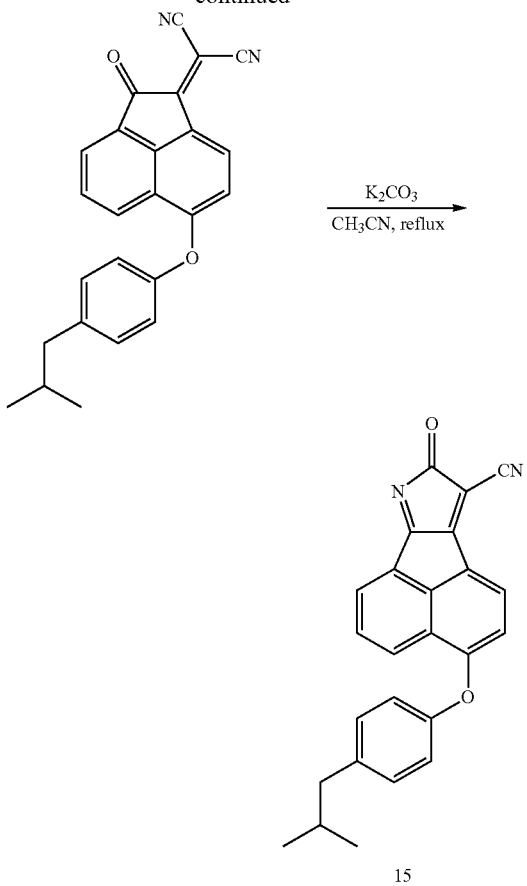

15

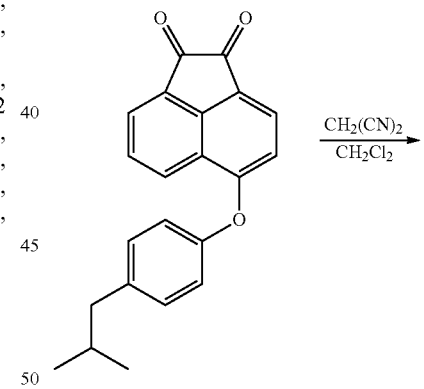

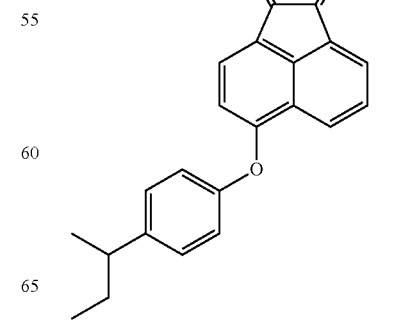

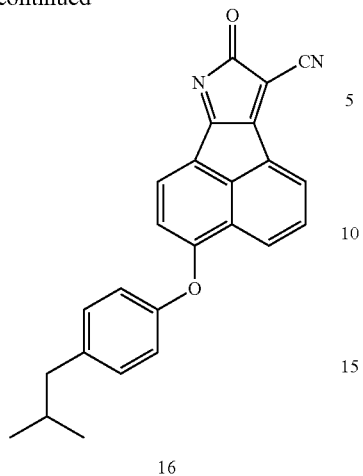

16

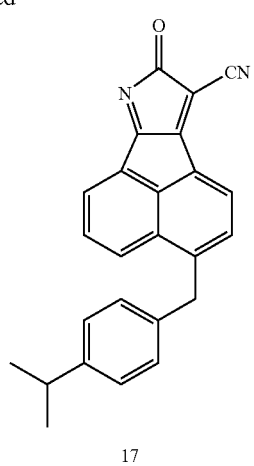

17

0.99 g 5-(4-Isopropyl-phenoxy)-acenaphthylene-1,2-dione and 0.33 g malononitrile were dissolved in dichloromethane, and then mixture was applied to a gel silica column and eluted quickly. After all the mixture passed through, the column was spun dry. Red solid was obtained with a weight of 1.07 g and a yield of 94%. 0.05 g of $K_2CO_3$ and 20 mL of acetonitrile were added into 0.77 g of the red solid. The mixture was heated and refluxed for 3 hours. After the reaction finished, the reaction solution was spun dry and separated by chromatographic column ($CH_2Cl_2$: petroleum ether=1:1) to obtain two isomers.

Characterization of 15: M.p. 214-215° C. $^1$H NMR (400 M, $CDCl_3$): δ 8.78 (d, J=7.6 Hz, 1H), 8.60 (d, J=8.0 Hz, 1H), 8.43 (d, J=7.6 Hz, 1H), 7.67 (t, J=8.0 Hz, 1H), 7.29 (d, J=8.0 Hz, 2H), 7.12 (d, J=8.0 Hz, 2H), 6.95 (d, J=8.0 Hz, 1H), 2.42 (d, J=8.0 Hz, 2H), 1.75 (m, 1H), 0.75 (d, J=8.0 Hz, 6H). TOF MS (EI$^+$): $C_{25}H_{18}N_2O_2$, (m/z): calcd for 378.1368, found 378.1365.

Characterization of 16: M.p. 273-274° C. $^1$H NMR (400 M, $CDCl_3$): δ 8.72 (d, J=7.6 Hz, 1H), 8.53 (d, J=8.0 Hz, 1H), 8.38 (d, J=7.6 Hz, 1H), 7.98 (t, J=8.0 Hz, 1H), 7.31 (d, J=8.0 Hz, 2H), 7.02 (d, J=8.0 Hz, 2H), 6.80 (d, J=8.0 Hz, 1H), 2.43 (d, J=8.0 Hz, 2H), 1.75 (m, 1H), 0.75 (d, J=8.0 Hz, 6H). TOF MS EI$^+$: $C_{25}H_{18}N_2O_2$, (m/z): calcd for 378.1368, found 378.1363.

EXAMPLE 15

Synthesis and Characterization of 3-(4-Isopropyl-phenoxy)-8-oxo-8H-acenaphtho[1,2-b]pyrrole-9-carbonitrile (17)

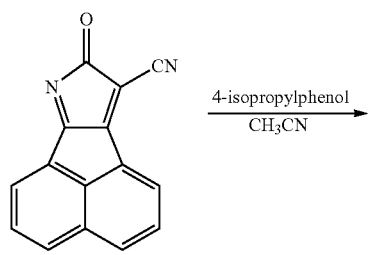

1 g 8-oxo-8H-acenaphtho[1,2-b]pyrrole-9-carbonitrile and 0.54 g 4-Isopropyl-phenol were dissolved in acetonitrile (50 ml), and then heated and refluxed for 3 hours. The solvent was reduced in vacuo and the residue was purified by normal phase column chromatography on silica gel with a yield of 30%.

Characterization of 3-(4-Isopropyl-phenoxy)-8-oxo-8H-acenaphtho[1,2-b]pyrrole-9-carbonitrile (17): M.p. 272-274° C.: $^1$H NMR (400 M, $CDCl_3$): δ 8.92 (d, J=8.0 Hz, 1H), 8.25 (d, J=8.8 Hz, 2H), 8.44 (d, J=8.0 Hz, 1H), 7.86 (t, J=8.0 Hz, 1H), 7.38 (d, J=8.4 Hz, 2H), 7.14 (d, J=8.4 Hz, 2H), 7.04 (d, J=8.8 Hz, 1H), 3.01 (m, 1H), 1.32 (d, J=8.0 Hz, 6H); TOF MS EI$^+$ (m/z): $C_{24}H_{16}N_2O_2$, calcd for 364.1212, found 364.1215.

EXAMPLE 16

Synthesis and Characterization of 3-(4-Isobutyl-phenylsulfanyl)-8-oxo-8H-acenaphtho[1,2-b]pyrrole-9-carbonitrile (18) and 4-(4-Isobutyl-phenylsulfanyl)-8-oxo-8H-acenaphtho[1,2-b]pyrrole-9-carbonitrile (19)

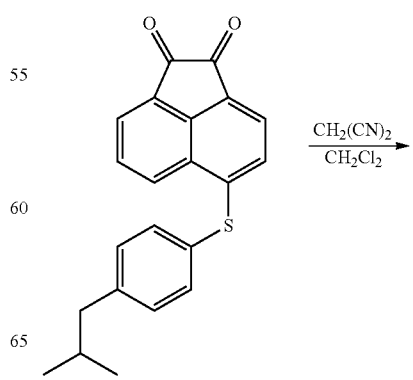

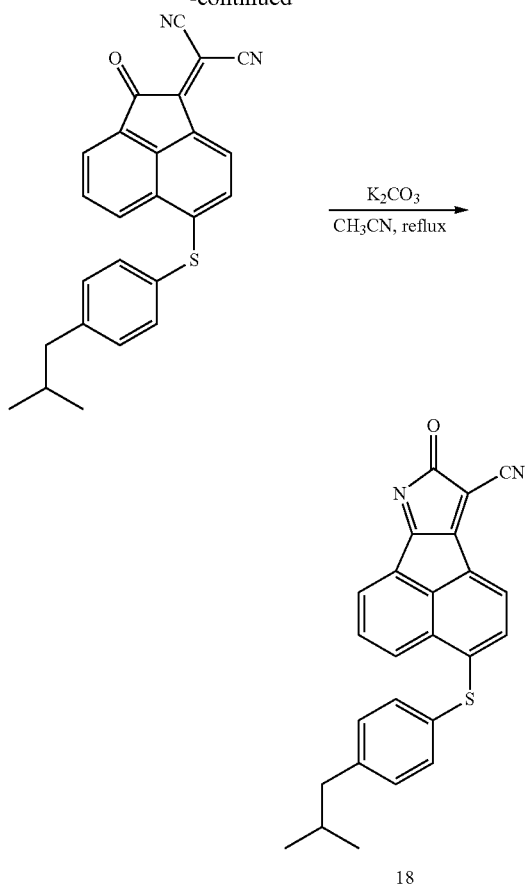

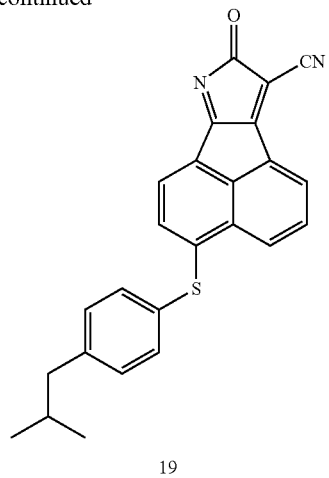

1.04 g 5-(4-Isobutyl-phenylsulfanyl)-acenaphthylene-1,2-dione and 0.33 g malononitrile were dissolved in dichloromethane, and then mixture was applied to a gel silica column and eluted quickly. After all the mixture passed through, the column was spun dry. Red solid was obtained with a weight of 0.99 g and a yield of 84%. 0.05 g of $K_2CO_3$ and 20 mL of acetonitrile were added into 0.79 g of the red solid. The mixture was heated and refluxed for 3 hours. After the reaction finished, the reaction solution was spun dry and separated by chromatographic column ($CH_2Cl_2$: petroleum ether=1:1) to obtain two isomers.

Characterization of 18: M.p. 234-235° C. $^1$H NMR (400M, $CDCl_3$): δ 8.58 (d, J=7.6 Hz, 1H), 8.41 (d, J=8.0 Hz, 1H), 8.30 (d, J=7.6 Hz, 1H), 7.53 (t, J=8.0 Hz, 1H), 7.31 (d, J=8.0 Hz, 2H), 7.02 (d, J=8.0 Hz, 2H), 6.95 (d, J=8.0 Hz, 1H), 2.75 (m, 1H), 1.69 (m, 2H), 1.29 (d, J=8.0 Hz, 3H), 0.92 (t, J=8.0 Hz, 3H). TOF MS (EI$^+$): $C_{25}H_{18}N_2OS$, (m/z): calcd for 394.1140, found 394.1142.

Characterization of 19: M.p. 282-283° C. $^1$H NMR (400M, $CDCl_3$): δ 8.55 (d, J=7.6 Hz, 1H), 8.39 (d, J=8.0 Hz, 1H), 8.15 (d, J=7.6 Hz, 1H), 7.92 (t, J=8.0 Hz, 1H), 7.45 (d, J=8.0 Hz, 2H), 7.13 (d, J=8.0 Hz, 2H), 7.02 (d, J=8.0 Hz, 1H), 2.75 (m, 1H), 1.69 (m, 2H), 1.29 (d, J=8.0 Hz, 3H), 0.92 (t, J=8.0 Hz, 3H). TOF MS EI$^+$: $C_{25}H_{18}N_2OS$, (m/z): calcd for 394.1140, found 394.1137.

EXAMPLE 17

Synthesis and Characterization of 3-(4-Isopropyl-phenylsulfanyl)-8-oxo-8H-acenaphtho[1,2-b]pyrrole-9-carbonitrile (20)

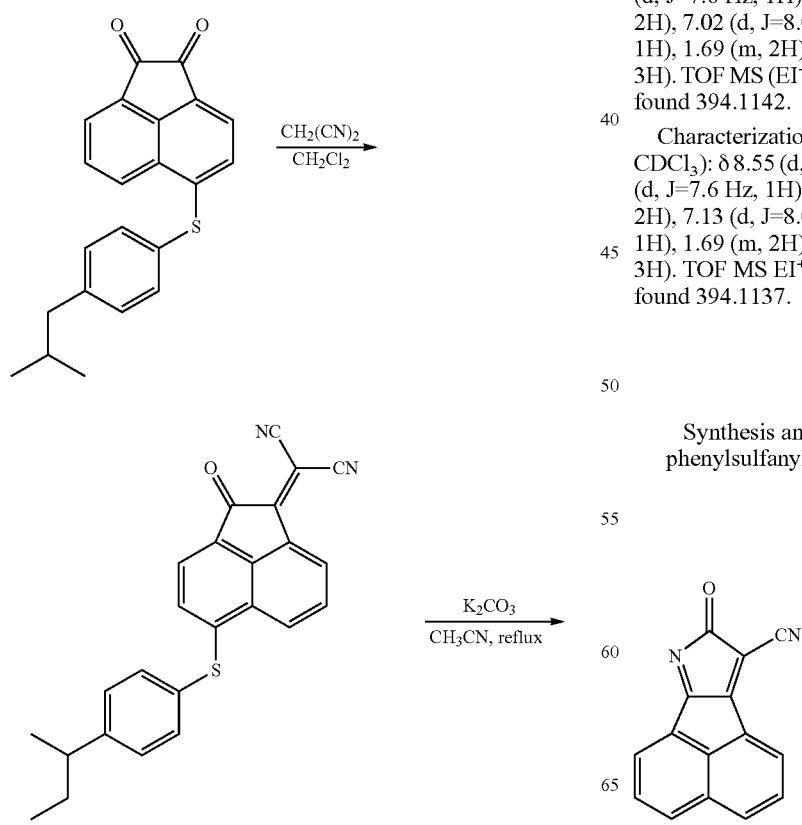

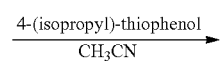

27

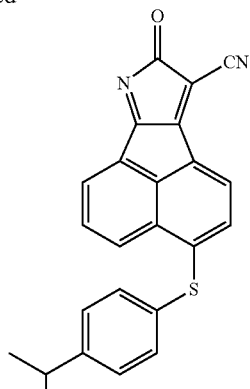

20

0.69 g 8-oxo-8H-acenaphtho[1,2-b]pyrrole-9-carbonitrile and 1.82 g 4-Isopropyl-benzenethiol were dissolved in acetonitrile (50 ml), and then stirred at room temperature for 3 h. The solvent was reduced in vacuo and the residue was purified by normal phase column chromatography on silica gel with a yield of 50%.

Characterization of 3-(4-Isopropyl-phenylsulfanyl)-8-oxo-8H-acenaphtho[1,2-b]pyrrole-9-carbonitrile (20): M.p. 214-215° C. $^1$H NMR (400 MHz, CDCl$_3$): δ 8.57 (d, J=8.4 Hz, 1H), 8.47 (d, J=8.4 Hz, 2H), 7.92 (d, J=8.0 Hz, 1H), 7.87 (d, J=8.0 Hz, 1H), 7.61 (t, J=8.0 Hz, 1H), 7.31 (t, J=9.2 Hz, 2H), 7.22 (d, J=8.4 Hz, 1H), 2.87 (m, 1H), 1.2 (d, J=8.0 Hz, 6H). TOF MS (EI$^+$): C$_{24}$H$_{16}$N$_2$OS, (m/z): calcd for 380.0983, found 380.0985.

EXAMPLE 18

Synthesis and Characterization of 3-(4-sec-Butyl-phenylsulfanyl)-8-oxo-8H-acenaphtho[1,2-b]pyrrole-9-carbonitrile (21)

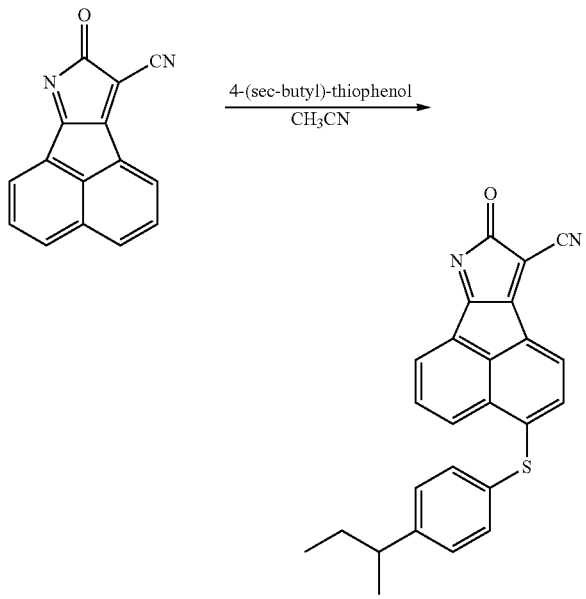

28

0.69 g 8-oxo-8H-acenaphtho[1,2-b]pyrrole-9-carbonitrile and 1.99 g 4-sec-Butyl-benzenethiol were dissolved in acetonitrile (50 ml), and then stirred at room temperature for 3 h. The solvent was reduced in vacuo and the residue was purified by normal phase column chromatography on silica gel with a yield of 42%.

Characterization of 3-(4-sec-Butyl-phenylsulfanyl)-8-oxo-8H-acenaphtho[1,2-b]pyrrole-9-carbonitrile (21): M.p. 245-246° C. $^1$H NMR (400M, CDCl$_3$): δ 8.85 (d, J=8.0 Hz, 1H), 8.22 (d, J=8.0 Hz, 1H), 8.07 (d, J=8.4 Hz, 1H), 7.68 (t, J=8.0 Hz, 1H), 7.53 (d, J=8.0 Hz, 2H), 7.41 (d, J=8.4 Hz, 2H), 7.12 (d, J=8.4 Hz, 1H), 2.55 (m, 1H), 1.55 (m, 2H), 1.31 (d, J=8.0 Hz, 3H), 0.89 (t, J=8.0 Hz, 3H). TOF MS (EI$^+$): C$_{25}$H$_{18}$N$_2$OS, (m/z): calcd for 394.1140, found 394.1137.

EXAMPLE 19

Synthesis and Characterization of 6-(4-Isopropyl-phenylsulfanyl)-8-oxo-8H-acenaphtho[1,2-b]pyrrole-9-carbonitrile (22)

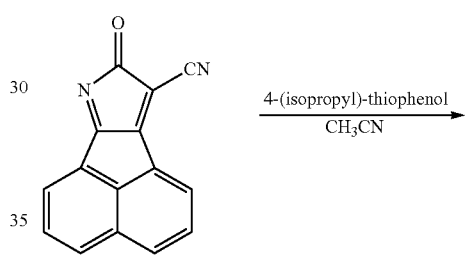

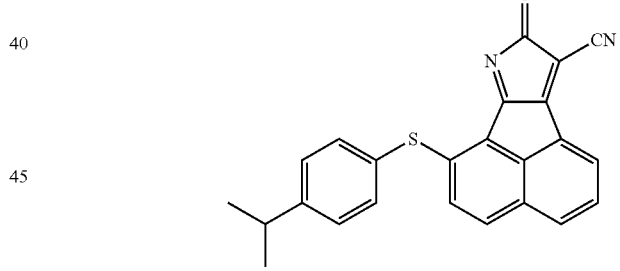

0.69 g 8-oxo-8H-acenaphtho[1,2-b]pyrrole-9-carbonitrile and 1.82 g 4-Isopropyl-benzenethiol were dissolved in acetonitrile (50 ml), and then stirred at room temperature for 3 h. The solvent was reduced in vacuo and the residue was purified by normal phase column chromatography on silica gel with a yield of 32%.

Characterization of 6-(4-Isopropyl-phenylsulfanyl)-8-oxo-8H-acenaphtho[1,2-b]pyrrole-9-carbonitrile (22): M.p. 257-259° C. 1H NMR (400M, CDCl$_3$): δ 8.32 (d, J=8.8 Hz, 1H), 8.11 (d, J=8.8 Hz, 1H), 7.95 (d, J=8.8 Hz, 1H), 7.85 (d, J=8.0 Hz, 1H), 7.57 (d, J=8.4 Hz, 2H), 7.50 (t, J=8.4 Hz, 1H), 7.06 (d, J=8.4 Hz, 2H), 2.87 (m, 1H), 1.2 (d, J=8.0 Hz, 6H). TOF MS EI$^+$: C$_{24}$H$_{16}$N$_2$OS, (m/z) calcd for 380.0983, found 380.0987.

EXAMPLE 20

Synthesis and Characterization of 3,6-Bis-(4-isopropyl-phenylsulfanyl)-8-oxo-8H-acenaphtho[1,2-b]pyrrole-9-carbonitrile (23)

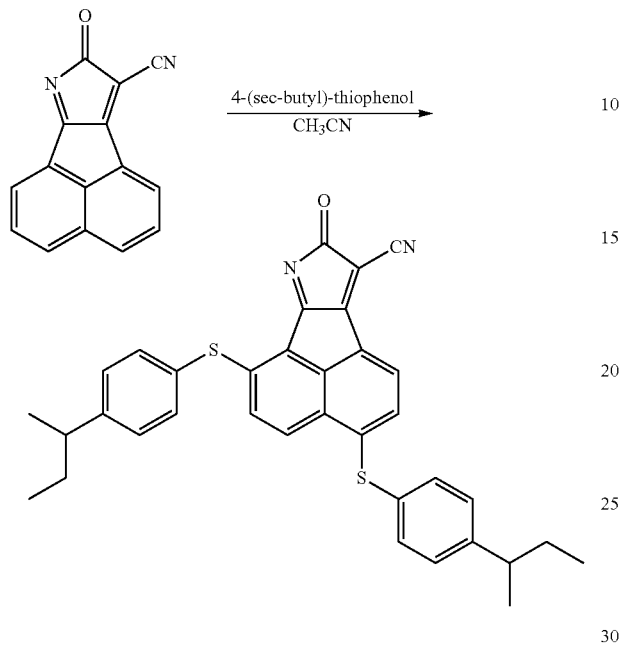

1.0 g 8-oxo-8H-acenaphtho[1,2-b]pyrrole-9-carbonitrile and 2.9 g 4-sec-Butyl-benzenethiol were dissolved in acetonitrile (50 ml), and then stirred at room temperature for 30 hours. The solvent was reduced in vacuo and the residue was purified by normal phase column chromatography on silica gel with a yield of 20%.

Characterization of 3,6-Bis-(4-isopropyl-phenylsulfanyl)-8-oxo-8H-acenaphtho[1,2-b]pyrrole-9-carbonitrile (23): M.p. 268-269° C. $^1$H NMR (400M, CDCl$_3$): δ 8.12 (d, J=8.8 Hz, 1H), 7.60 (d, J=8.8 Hz, 1H), 7.51 (d, J=8.0 Hz, 4H), 7.48 (d, J=8.8 Hz, 1H), 7.23 (d, J=8.8 Hz, 1H), 7.08 (d, J=8.0 Hz, 4H), 2.55 (m, 2H), 1.52 (m, 4H), 1.25 (d, J=8.0 Hz, 6H), 0.78 (t, J=8.0 Hz, 6H). TOF MS EI$^+$: C$_{35}$H$_{30}$N$_2$OS$_2$, (m/z): calcd for 558.1800, found 558.1803.

EXAMPLE 21

Synthesis and Characterization of 3-(4-Aminomethyl-benzoyl)-8-oxo-8H-acenaphtho[1,2-b]pyrrole-9-carbonitrile (24) and 4-(4-Aminomethyl-benzoyl)-8-oxo-8H-acenaphtho[1,2-b]pyrrole-9-carbonitrile (25)

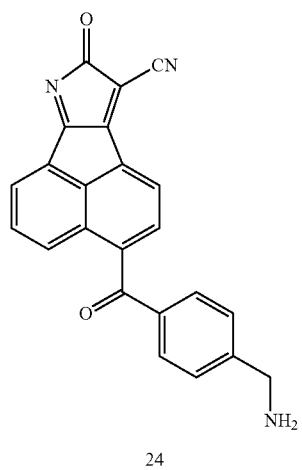

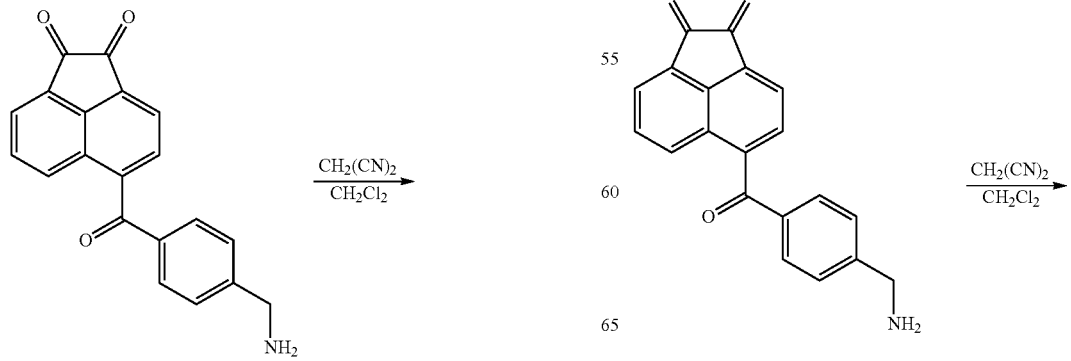

-continued

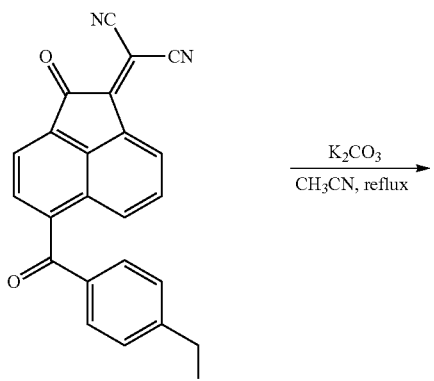

EXAMPLE 22

Synthesis and Characterization of 3-Hexyloxy-8-oxo-8H-acenaphtho[1,2-b]pyrrole-9-carboxylic acid (26)

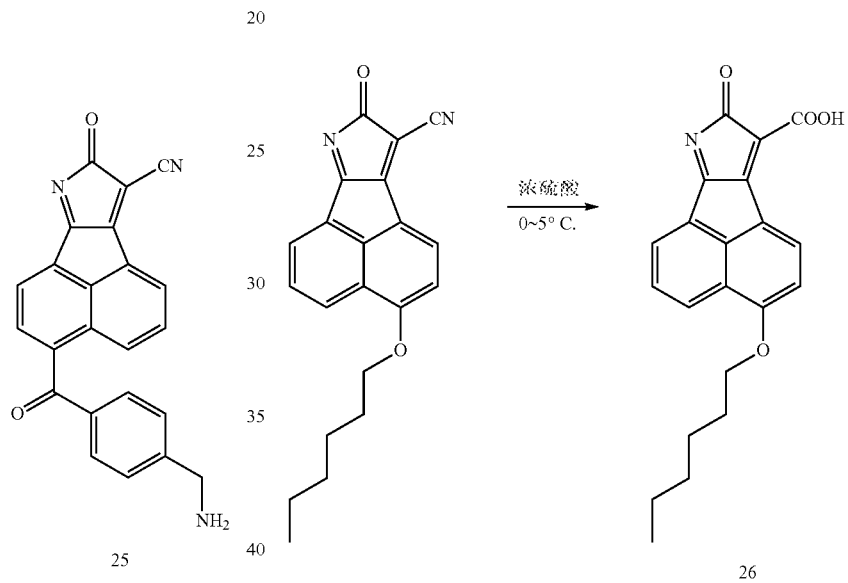

0.95 g 5-(4-Aminomethyl-benzoyl)-acenaphthylene-1,2-dione and 0.33 g malononitrile were dissolved in dichloromethane, and then mixture was applied to a gel silica column and eluted quickly. After all the mixture passed through, the column was spun dry. Dark red solid was obtained with a weight of 0.93 g and a yield of 85%. 0.08 g of $K_2CO_3$ and 20 mL of acetonitrile were added into 0.73 g of the dark red solid. The mixture was heated and refluxed for 3 hours. After the reaction finished, the reaction solution was spun dry and separated by chromatographic column ($CH_2Cl_2$: petroleum ether=2:1) to obtain dark red solid. The isomer ratio is 1:0.2 tested by nuclear magnetic resonance. The resulting isomers were separated by liquid phase separation to obtain two isomers.

Characterization of 24: M.p. 289-290° C. $^1$H NMR (400M, $CDCl_3$): δ 8.96 (dd, J=8.8 Hz, 1H), 8.73 (d, J=8.8 Hz, 1H), 8.15 (d, J=8.4 Hz, 1H), 8.08 (t, J=8.8 Hz, 1H), 7.93 (d, J=8.4 Hz, 1H), 7.69 (d, J=8.4 Hz, 2H), 7.35 (d, J=8.4 Hz, 2H), 6.32 (br, 2H), 4.36 (s, 2H). TOF MS EI$^+$: $C_{23}H_{13}N_3O_2$, (m/z): calcd for 363.1008, found 363.1009.

Characterization of 25: M.p.>300° C.: $^1$H NMR (400M, $CDCl_3$): δ 8.85 (dd, J=8.8 Hz, 1H), 8.70 (d, J=8.8 Hz, 1H), 8.10 (d, J=8.4 Hz, 1H), 7.98 (t, J=8.8 Hz, 1H), 7.86 (d, J=8.4 Hz, 1H), 7.59 (d, J=8.4 Hz, 2H), 7.50 (d, J=8.4 Hz, 2H), 6.08 (br, 2H), 4.36 (s, 2H). TOF MS EI$^+$: $C_{23}H_{13}N_3O_2$, (m/z): calcd for 363.1008, found 363.1005.

60 ml of concentrated sulfuric acid or 25 ml of fuming sulfuric acid was added into a 50 ml single neck flask. 0.05 mol of 3-Hexyloxy-8-oxo-8H-acenaphtho[1,2-b]pyrrole-9-carbonitrile was added thereinto in batches at a temperature of 0-5° C. within 1 hour. After that, the reaction was carried out for another 18 hours at room temperature, and the resulting reaction mixture was viscous, deep, brownish red. Then the resulting mixture was dropped slowly into crushed ice and stirred acutely. After that, the mixture was stood and filtered. The filter cake was washed with a great quantity of water until it became neutral. The filter cake was dried to obtain the product with a yield of 90%.

Characterization of 3-Hexyloxy-8-oxo-8H-acenaphtho[1,2-b]pyrrole-9-carboxylic acid (26): M.p. 235-237° C. $^1$H NMR (400M, $CDCl_3$): δ 11.0 (s, 1H), 8.55 (d, J=8.0 Hz, 1H), 8.45 (d, J=8.0 Hz, 1H), 8.01 (t, J=8.0 Hz, 1H), 7.71 (d, J=8.4 Hz, 1H), 6.561 (d, J=8.4 Hz, 1H), 4.10 (t, J=7.6 Hz, 2H), 1.75 (m, J=7.6 Hz, 2H), 1.43 (m, 2H), 1.31 (m, 2H), 1.29 (m, 2H), 0.89 (t, J=7.6 Hz, 3H); TOF MS EI$^+$: $C_{21}H_{19}NO_4$, (m/z): calcd for 349.1314, found 349.1316.

EXAMPLE 23

Synthesis and Characterization of 3-(4-Isobutyl-phenoxy)-8-oxo-8H-acenaphtho[1,2-b]pyrrole-9-carboxylic acid methyl ester (27)

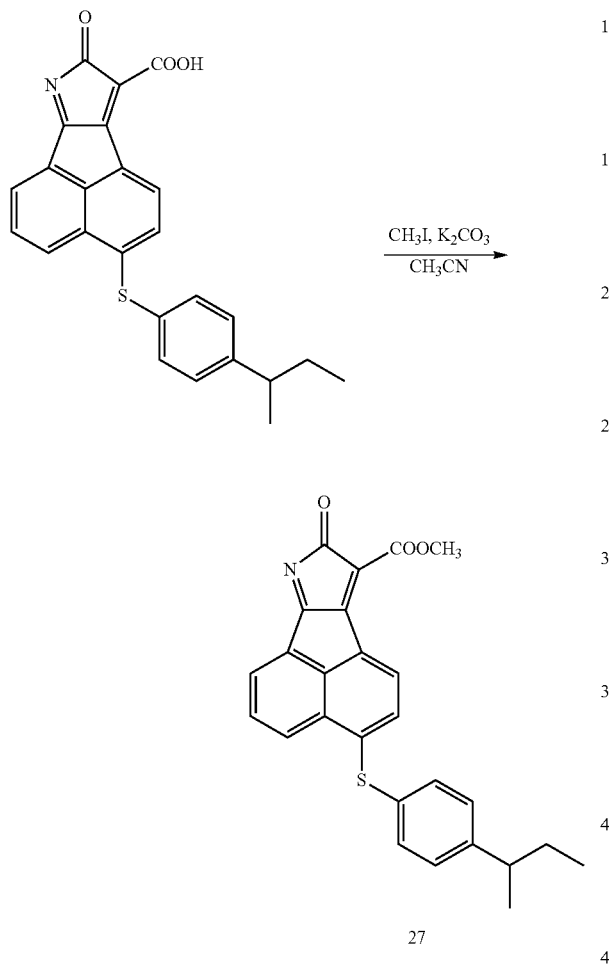

3.78 g of 3-4-Isobutyl-phenoxy-8-oxo-8H-acenaphtho[1,2-b]pyrrole-9-carboxylic acid, 50 ml of acetonitrile as solvent, 2.76 g of $K_2CO_3$ as deacid reagent and iodomethane over ten times were added into a 100 ml single neck flask in sequence. Under nitrogen protection, the mixture was heated up to 42° C. and the reaction was lasted for 18 hours. The acetonitrile was vaporized out under decompressed condition, and the reactant was fully dissolved by addition of dichloromethane. After filtration, the filtrate was spun dry to obtain a yellow brown crude product. The deep yellow product was obtained by column chromatographic separation with gel silica with the yield 85%.

Characterization of 3-(4-Isobutyl-phenoxy)-8-oxo-8H-acenaphtho[1,2-b]pyrrole-9-carboxylic acid methyl ester (27): M.p. 215-216° C. $^1$H NMR (400M, CDCl$_3$): δ 8.45 (d, J=8.0 Hz, 1H), 8.35 (d, J=8.0 Hz, 1H), 7.85 (t, J=8.0 Hz, 1H), 7.68 (d, J=8.4 Hz, 1H), 7.36 (d, J=8.8 Hz, 2H), 7.23 (d, J=8.8 Hz, 2H), 6.50 (d, J=8.4 Hz, 1H), 2.45 (d, J=8.4 Hz, 2H), 1.52 (m, 2H), 1.25 (d, J=8.4 Hz, 3H), 0.93 (t, J=8.4 Hz, 3H). TOF MS EI$^+$: $C_{26}H_{21}N_3O_3S$, (m/z): calcd for 427.1242, found 427.1245.

EXAMPLE 24

Synthesis and Characterization of 3-(4-Isobutyl-phenoxy)-8-oxo-8H-acenaphtho[1,2-b]pyrrole-9-carboxylic acid butylamide (28)

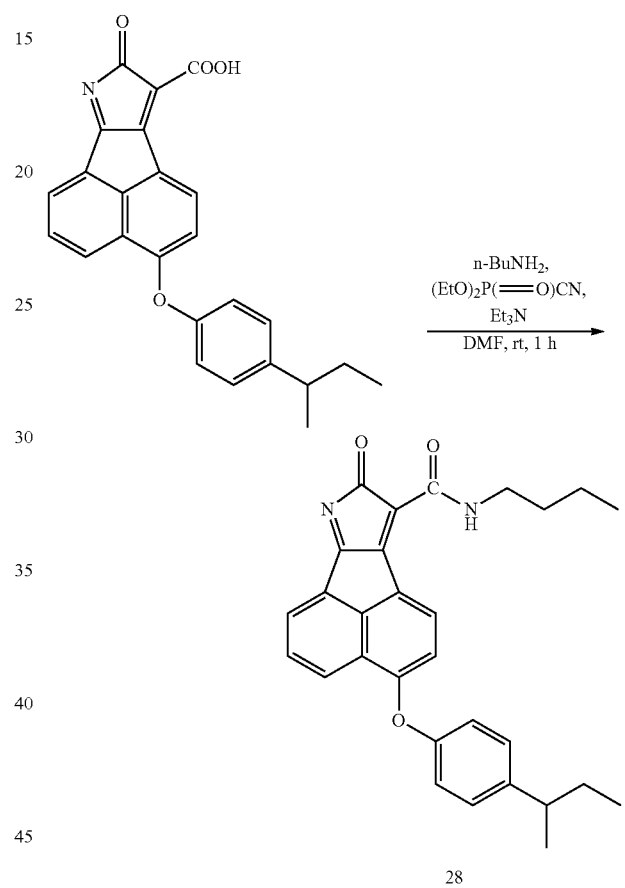

3.97 g of 3-(4-Isobutyl-phenoxy)-8-oxo-8H-acenaphtho[1,2-b]pyrrole-9-carboxylic acid, 50 ml of DMF as solvent, 0.15 mL of triethylamine, 1.63 g of (EtO)$_2$P(=O)CN and n-butylamide over ten times were added into a 100 ml single neck flask in sequence and reacted for 1 hour at room temperature. Then yellow solid was obtained after the reaction finished. The yield was 85%.

Characterization of 3-(4-Isobutyl-phenoxy)-8-oxo-8H-acenaphtho[1,2-b]pyrrole-9-carboxylic acid butylamide (28): M.p. 247° C. $^1$H NMR (400M, CDCl$_3$): δ 8.49 (d, J=8.0 Hz, 1H), 8.40 (d, J=8.0 Hz, 1H), 7.83 (t, J=8.0 Hz, 1H), 7.66 (d, J=8.0 Hz, 1H), 7.46 (d, J=8.4 Hz, 2H), 7.31 (d, J=8.4 Hz, 2H), 6.63 (d, J=8.0 Hz, 1H), 5.53 (br, 1H), 3.21 (t, J=8.0 Hz, 2H), 2.53 (m, 1H), 1.52-1.50 (m, 7H), 1.25-1.32 (m, 5H), 0.91 (t, J=8.0 Hz, 3H). TOF MS EI$^+$: $C_{25}H_{19}N_2O_3$, (m/z): calcd for 395.1396, found 395.1394.

Part II: Detection of the Physicochemical Bioactivity of the Bcl-2 Inhibitors

EXAMPLE 13

Detection of BH3 Analogous Degree of the Compounds by ELISA Assay

The present inventors used fluorescence polarization assay to detect the bonding force between the protein and the compounds in a previous study (PCT/CN2010/075521). The data of the following studies showed that the fluorescent tag FAM was interfered by the compounds because of the autofluorescence in the fluorescence polarization assay. ELISA assay was used to detect the bonding force between the compounds and the protein in this application.

Biotinylated Bim peptide was diluted to 0.09 μg/mL in SuperBlock blocking buffer in PBS and incubated for 1.5 h in 96-well microtiter plates already coated with streptavidin to allow the formation of the complex between Biotin-Bim and streptavidin. All incubations were performed at room temperature unless otherwise noted. Each inhibitor was first dissolved in pure DMSO to obtain a 10 mM stock solution. For each tested inhibitor, different concentrations of the inhibitor were incubated with 20 nM His-tagged Mcl-1 protein in PBS for 1 h with a final DMSO concentration of 4%. The plates were washed three times with PBS containing 0.05% Tween-20. The inhibitor and protein mixture (100 μL) were transferred to the plate containing the biotin-Bim/streptavidin complex and incubated for 2 h. The plate was then washed as before and mouse anti-His antibody that conjugated with horseradish peroxidase was added into the wells and incubated for 1 h. The plate was then washed with PBS containing 0.05% Tween-20. Finally, TMB was added to each well; the enzymatic reaction was stopped after 30 min by addition of $H_2SO_4$ (100 μL, 2M). Absorbances were measured with a TECAN GENios (Swiss, TECAN) microplate reader using a wavelength of 450 nm. Three independent experiments were performed with each inhibitor to calculate average $IC_{50}$ value and standard deviation (SD).

The BH3 analogous degrees of other 11 compounds were detected by using the experimental method as described above. The protein binding constant (binding constant in table 1) between them and Bcl-2 and Mcl-1 proteins were also on nM grade. The detailed results were shown in table 1.

TABLE 1

| Compound | Bcl-2 binding constants (nM) | Mcl-1 binding constants (nM) |
|---|---|---|
| 1 | 142 | 49 |
| 2 | 28 | 25 |
| 3 | 8 | 14 |
| 4 | 35 | 95 |
| 5 | 65 | 125 |
| 6 | 45 | 66 |
| 7 | 66 | 14 |
| 8 | 6 | 4 |
| 9 | 63 | 16 |
| 10 | 17 | 5 |
| 11 | 112 | 46 |
| 12 | 9 | 15 |

The binding capacities between the compounds and protein in this application are significantly greater than the binding capacities in previous studies about a series of acenaphtho heterocyclic compounds of 8-oxo-8H-acenaphtho[1,2-b]pyrrole-9-carbonitrile (WO2010054575A1; CN101423491A; J. Med. Chem, 2011, 54, 1101-1105; E J. Med Chem, doi: 10.1016/j.ejmech. 2011.05.062). Spss software was used to do statistical analysis, the results showed that $p<0.05$. This result indicated that the Bcl-2 protein binding constant of a series of compounds in this application were significantly lower than the corresponding value of the series acenaphtho heterocyclic compounds which have been disclosed in the prior studies under existing technical conditions. The Mcl-1 protein binding constant of a series of compounds in this application were significantly lower than the corresponding value of the acenaphtho heterocyclic compounds which have been disclosed in the prior studies under existing technical conditions.

EXAMPLE 14

Detection of BH3 Analogous Degree of the Compounds by Fluorescence Polarization Assay A Bid BH3 peptide (amino acids: 79-99: QEDIIRNIAR-HLAQVGDSMDR) having 21 amino acids was synthesized and marked with 6-carboxyfluorescein N-succinimidyl ester (FAM) as fluorescent tag (FAM-Bid) at the N-terminal. The reaction system used in the competitive binding experiment was GST-Bcl-2 protein (40 nM) or Mcl-1 protein, which was dissolved in the reaction buffer (100 mM $K_3PO_4$, pH 7.5; 100 μg/ml bovine γ albumin; 0.02% sodium azide) together with FAM-Bid polypeptide (5 nM). In a 96-well plate, 100 4 of the reaction system was added into each well. Then 1 μL different concentration of compound 13 mother solution to be detected dissolved in DMSO was added there into until the final concentration met the experimental design requirements. Meanwhile, two control groups were established, one with the reaction system only containing Bcl-2 or Mcl-1 and FAM-Bid (equivalent to 0% inhibition rate), the other with the reaction system only containing FAM-Bid peptide. After 4 hours of incubation, the 96-well plate was detected by enzyme-labelled meter. The fluorescent polarization value (mP) was tested at 485 nm emission wavelength excited and generated by 530 nm wavelength. $K_i$ value was deduced according to calculation formula. The experimental results were shown in FIGS. 3 and 4. The competitive binding constant between the compound and Bcl-2 was 158 nM. The competitive binding constant between the compound and Mcl-1 was 24 nM.

The BH3 analogous degrees of other 12 compounds were detected by using the experimental method as described above. The protein binding constant (binding constant in table 2) between them and Bcl-2 and Mcl-1 proteins were also on nM grade. The detailed results were shown in table 2.

TABLE 2

| Compound | Bcl-2 binding constants (nM) | Mcl-1 binding constants (nM) |
|---|---|---|
| 13 | 158 | 24 |
| 15 | 140 | 12 |
| 16 | 210 | 56 |
| 17 | 20 | 85 |
| 18 | 120 | 8 |
| 19 | 23 | 85 |
| 20 | 23 | 57 |
| 21 | 12 | 65 |
| 22 | 9 | 85 |
| 23 | 540 | 25 |
| 25 | 115 | 135 |
| 26 | 105 | 85 |
| 27 | 86 | 75 |

EXAMPLE 15

Detection of the BH3 Analogous Degree of the Compounds by Intracellular Fluorescence Polarization Energy Transfer (FRET)

2 μg of Bcl-2-CFP and Bax-YFP plasmids were transfected separately or simultaneously into Hela cells by using calcium phosphate coprecipitation method, 24 hours later, the cells were inoculated in a 6-well plate ($2\times10^5$ cells/well), and the compound 1 to be detected dissolved in DMSO was added there into until the final concentration (2, 5, 10 and 15 μM) was achieved. 24 hours later (please refer to FIG. 5); the cells were washed with PBS for three times. The fluorescence value was detected by GENIOS fluorescence enzyme-labelled meter (TECAN, Swiss). In time-dependent experiment, the transfected cells were inoculated in a 6-well plate, after that, 40 μM of the compound was added thereinto. 3, 6 and 24 hours later (FIG. 6), the fluorescence intensities were detected by plate reader. As for the cell group in which only Bcl-2-CFP plasmid was transfected, the values at 475 nm emission wave length and 433 nm excitation wave length were recorded. As for the cell group in which only Bax-YFP plasmid was transfected, the values at 527 nm emission wave length and 505 nm excitation wave length were recorded. As for the cell group in which Bcl-2-CFP and Bax-YFP plasmids were co-transfected, the values at 527 nm and 475 emission wave lengths and 433 nm excitation wave length were recorded. The ratio of fluorescence intensity at 527 nm and 475 nm emission wave lengths was FRET. The FRET for the control group in which the plasmid was solely transfected was set as 1.0. This meant that the fluorescence polarization energy transfer for two proteins did not occur. In the cotransfected cells, the FRET increased up to 2.0 due to the interaction of Bcl-2 protein and Bax protein, and that the interference to the interaction between the two proteins increased and FRET decreased with the increase of the drug concentration and time. The cellular vitality was detected by MTT method. The experimental results were shown in FIGS. 5 and 6. When the concentration of the compound reached 1 μM, the interaction between Bcl-2 and Bax can be interfered after 2 hours, and the results appeared concentration-time dependent trend.

Other 24 compounds were detected by the same experimental method as described above, it has been experimentally proved that all the compounds had the function of simulating BH3-only protein in cells and can obviously interfere with the interaction between Bcl-2 and Bax under different concentration and time conditions. The detailed results were shown in table 3.

Wherein the concentration and time meant that the detected compound interfered with the interaction between Bcl-2 and Bax at the concentration for the time period.

TABLE 3

| Compound | Doses (μM) | Time (h) |
|---|---|---|
| 1 | 1.0 | 2 |
| 2 | 0.4 | 3 |
| 3 | 0.2 | 2 |
| 4 | 1.0 | 5 |
| 5 | 2.0 | 6 |
| 6 | 2.0 | 5 |
| 7 | 0.3 | 3 |
| 8 | 0.1 | 1 |
| 9 | 0.4 | 2 |
| 10 | 0.1 | 2 |
| 11 | 0.3 | 2 |
| 12 | 0.2 | 1 |
| 13 | 0.5 | 4 |
| 15 | 0.5 | 4 |
| 16 | 0.5 | 3 |
| 17 | 0.1 | 2 |
| 18 | 0.5 | 4 |
| 19 | 0.3 | 3 |
| 20 | 0.2 | 2 |
| 21 | 0.2 | 2 |
| 22 | 0.5 | 2 |
| 23 | 1.0 | 2 |
| 25 | 0.6 | 4 |
| 26 | 0.5 | 5 |
| 27 | 0.3 | 3 |

EXAMPLE 16

Figure 8:
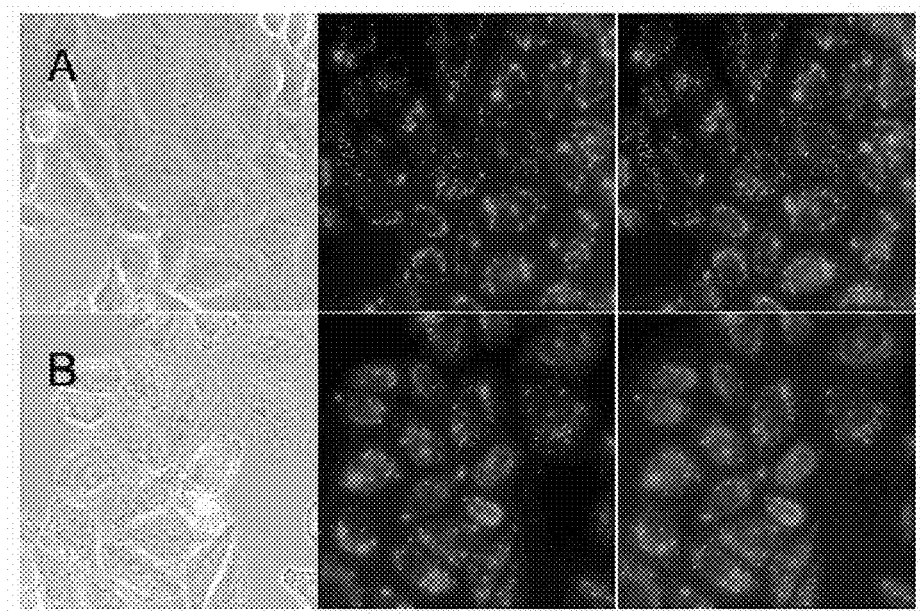
FIG. 8 shows the negative results of BH3 analogous degree of the compound 1 detected by Bax protein and mitochondria co-localization.

Detection of the BH3 Analogous Degree of the Compounds by Co-Localization Between Bax Protein and Chondriosome 5 μg of Bax-YFP plasmid was transfected into MCF-7 cells by using calcium phosphate coprecipitation method, 24 hours later, the cells were inoculated in a 6-well plate ($0.2\times10^6$ cells/well), and 10 μM of the compound 1 to be detected was added thereinto. 6 hours later, the cells were washed with PBS and hatched away from light with 50 nM Mito Tracker Red CMXRos (chondriosome specific probes; red) for 10 minutes. Then the cells were washed with PBS for three times, and the fluorescent image was scanned with Radiance2000 laser confocal microscopy (Bio-Rad, USA). Meanwhile, dual channel scanning was carried out, one channel was used to scan the green fluorescence of Bax-YFP, and the other channel was used to scan the red fluorescence of the CMXRos probe for indicating the chondriosome. The co-localization circumstance was displayed by superimposing the two channel images. When the Bax protein was localized on the chondriosome, the green and red fluorescence was superimposed into orange, as shown in FIG. 7. FIG. 8 for comparison showed that the BAX cannot be drived to shift towards the chondriosome, i.e., the co-localization failed.

Other 24 compounds were detected by the same experimental method as described above. The results showed that all the compounds had the function of driving the BAX to shift towards the chondriosome, which indicated that they all had the function of simulating the BH3-only protein in cells. The detailed results were shown in table 4. Wherein the concentration and time meant that the detected compound simulated the BH3-only protein and driven the BAX to shift towards the chondriosome at the concentration for the time period.

TABLE 4

| Compound | Doses (μM) | Time (h) |
|---|---|---|
| 1 | 1.0 | 3 |
| 2 | 0.5 | 3 |
| 3 | 0.2 | 2 |
| 4 | 3.0 | 4 |
| 5 | 5.0 | 5 |
| 6 | 4.0 | 4 |
| 7 | 0.5 | 3 |
| 8 | 0.1 | 1 |
| 9 | 0.6 | 3 |
| 10 | 0.2 | 1 |
| 11 | 0.9 | 3 |

TABLE 4-continued

| Compound | Doses (μM) | Time (h) |
|---|---|---|
| 12 | 0.3 | 2 |
| 13 | 5.0 | 4 |
| 15 | 5.0 | 3 |
| 16 | 4.0 | 3 |
| 17 | 1.0 | 1 |
| 18 | 5.0 | 4 |
| 19 | 3.0 | 3 |
| 20 | 5.0 | 3 |
| 21 | 2.0 | 2 |
| 22 | 5.0 | 3 |
| 23 | 1.0 | 3 |
| 25 | 6.0 | 4 |
| 26 | 5.0 | 5 |
| 27 | 2.0 | 3 |

EXAMPLE 17

Experimental Testing for the Property of the BH3 Analogues by the Cytotoxicity of the Compounds Depending on BAX/BAK 3 μg of BAX/BAK interfering plasmid was transfected into MCF-7 cells by using calcium phosphate coprecipitation method, 24 hours later, the cells were collected. The expressions after the BAX and BAK proteins interfered with RNA was detected by Western, and the cell groups without plasmid transfection were treated similarly and were set as the control group. The transfected cells were inoculated in a 96-well plate ($1 \times 10^5$ cells/well), the control experiment of the cell group without plasmid transfection was carried out in parallel. The compound 1 to be detected was added thereinto according to the concentration gradient designed before the experiment. 48 hours later, the cellular vitality was detected by MTT. The experimental results were shown in FIG. 9, Gossypol as nonspecific BH3 analogue was treated in parallel. The results showed that compound 1 had cytotoxicity of absolute dependence on BAX/BAK.

Other 24 compounds were also detected by the same experimental method as described above, the differences of $IC_{50}$ values between the transfected cells and the without plasmid transfection cells were compared. Results showed that the detected compounds also had the characteristics of absolute dependence on BAX/BAK.

TABLE 5

| Compound | $IC_{50}$ value in untransfected cells (μM) | $IC_{50}$ value in transfected cells (μM) |
|---|---|---|
| 1 | 4 | >50 |
| 2 | 3.5 | >50 |
| 3 | 3 | >50 |
| 4 | 5.6 | >50 |
| 5 | 6.5 | >50 |
| 6 | 4.0 | >50 |
| 7 | 1.2 | >50 |
| 8 | 1.0 | >50 |
| 9 | 1.3 | >50 |
| 10 | 0.5 | >50 |
| 11 | 4.2 | >50 |
| 12 | 2.9 | >50 |
| 13 | 7.5 | >50 |
| 15 | 7.1 | >50 |
| 16 | 8.5 | >50 |
| 17 | 2 | >50 |
| 18 | 6.8 | >50 |
| 19 | 2.2 | >50 |
| 20 | 2.1 | >50 |
| 21 | 1.5 | >50 |
| 22 | 1.2 | >50 |
| 23 | 15 | >50 |
| 25 | 6.5 | >50 |
| 26 | 6.2 | >50 |
| 27 | 5.6 | >50 |

EXAMPLE 18

Detection of the Inhibition of the Compounds Against Md-1 and Bcl-2 by Western Blotting (1) The cell sample was collected and cracked with $1 \times 10^6$/50 μl cell lysis solution (62.5 mM Tris-HCL pH 6.8; 2% SDS; 10% glycerol; 50 mM DTT; 0.01% bromphenol blue) at low temperature, then the solution was centrifuged and the protein supernatant was collected. The sample was boiled at 100° C. for 5 minutes and then was separated by electrophoresis on 12% SDS-PAGE and transferred. The interest protein was detected by the corresponding antibody. The expression of the interest protein in the cells was detected by horseradish peroxidase-labeled secondary antibodies in combination with ECL coloration method. The inhibition of the compound 1 to be detected against Mcl-1 and Bcl-2 was separately shown in FIG. 10 and FIG. 11. It can be seen from the figures that the Bcl-2 and Mcl-1 protein bands gradually became light as the time for the compound to be detected acting on the tumor cells went. This meant that the compound had the inhibition against these two proteins. The concentration of the protein bands in the Western images were carried out semi-quantitative analysis and normalization treatment with KODAK Gel Logic 1500 imaging system software. The concentration of the protein bands was shown in FIG. 12 and FIG. 13.

The following 18 compounds were also detected by using the same method as described above, it can be seen that they all had the inhibition against Bcl-2 and Mcl-1 proteins. Bcl-2 and Mcl-1 were inhibited by these compounds and the results of the semiquantitative analysis were shown in Table 6 and 7:

TABLE 6

| Compound | Control | 6 h | 12 h | 18 h | 24 h |
|---|---|---|---|---|---|
| 1 | 1 | 0.99 | 0.99 | 0.58 | 0.21 |
| 2 | 1 | 0.99 | 0.99 | 0.50 | 0.19 |
| 3 | 1 | 0.99 | 0.99 | 0.49 | 0.18 |
| 7 | 1 | 0.99 | 0.99 | 0.51 | 0.20 |
| 8 | 1 | 0.99 | 0.99 | 0.42 | 0.10 |
| 9 | 1 | 0.99 | 0.99 | 0.49 | 0.20 |
| 10 | 1 | 0.99 | 0.99 | 0.45 | 0.12 |
| 11 | 1 | 0.99 | 0.99 | 0.57 | 0.22 |
| 12 | 1 | 0.99 | 0.99 | 0.45 | 0.16 |
| 13 | 1 | 0.99 | 0.99 | 0.42 | 0.14 |
| 15 | 1 | 0.99 | 0.99 | 0.39 | 0.12 |
| 17 | 1 | 0.99 | 0.99 | 0.58 | 0.11 |
| 18 | 1 | 0.99 | 0.99 | 0.36 | 0.10 |
| 20 | 1 | 0.99 | 0.99 | 0.50 | 0.23 |
| 21 | 1 | 0.99 | 0.99 | 0.49 | 0.18 |
| 22 | 1 | 0.99 | 0.99 | 0.60 | 0.37 |
| 23 | 1 | 0.99 | 0.99 | 0.70 | 0.41 |
| 27 | 1 | 0.99 | 0.99 | 0.57 | 0.29 |

TABLE 7

| Compound | Control | 2 h | 6 h |
| --- | --- | --- | --- |
| 1 | 1 | 0.79 | 0.35 |
| 2 | 1 | 0.70 | 0.31 |
| 3 | 1 | 0.65 | 0.29 |
| 7 | 1 | 0.68 | 0.32 |
| 8 | 1 | 0.52 | 0.22 |
| 9 | 1 | 0.60 | 0.29 |
| 10 | 1 | 0.53 | 0.21 |
| 11 | 1 | 0.70 | 0.34 |
| 12 | 1 | 0.66 | 0.28 |
| 13 | 1 | 0.79 | 0.29 |
| 15 | 1 | 0.69 | 0.42 |
| 17 | 1 | 0.65 | 0.37 |
| 18 | 1 | 0.66 | 0.39 |
| 20 | 1 | 0.60 | 0.29 |
| 21 | 1 | 0.59 | 0.28 |
| 22 | 1 | 0.68 | 0.49 |
| 23 | 1 | 0.60 | 0.59 |
| 27 | 1 | 0.57 | 0.29 |

The invention claimed is:

1. An acenaphtho heterocyclic compound of Formula I:

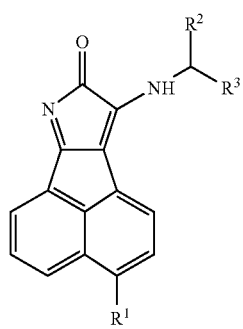

I wherein:
$R^1$ is selected from the group consisting of H, thiomorpholinyl and $XR^4$;
$R^2$ is selected from the group consisting of $(CH_2)_nZ$ and $(CH_2)_nPh-(o,m,p)Z$; Z is selected from the group consisting of $NO_2$, Ph, $CF_3$, $OCH_3$, $SCH_3$, $NH_2$, $NHCH_3$, $N(CH_3)_2$, and straight or branched $C_{1-8}$ alkyl that is unsubstituted or substituted by halogen, amino, hydroxyl, ester or carboxyl;
$R^3$ is $(CH_2)_nW$, wherein W is selected from the group consisting of H, CN, $NO_2$, $NH_2$, COOH, CHO, OH, and $SO_3H$;
$R^4$ is selected from the group consisting of $(CH_2)_nY$, thenoyl, tetrahydropyrane, tetrahydrothiapyran, and $(CH_2)_nPh-(o,m,p)Y$, Y is a straight or branched $C_{1-8}$ alkyl that is unsubstituted or substituted by halogen, amino, hydroxyl, ester or carboxyl;
X is O, S, amino, carbonyl, ester, amide or sulfamide;
n is 0 to 4.

2. The compound according to claim 1, wherein Z is a straight or branched $C_{1-4}$ alkyl that is unsubstituted or substituted.

3. The compound according to claim 2, wherein $R^2$ is $(CH_2)_nPh-(o,m,p)Z$, Z is a straight or branched $C_{1-3}$ alkyl that is unsubstituted or substituted.

4. The compound according to claim 1, wherein W is H, $NH_2$ or OH.

5. The compound according to claim 4, wherein X is O or S.

6. The compound according to claim 5, wherein $R^4$ is $(CH_2)_nY$, Y is selected from the group consisting of Ph, $CF_3$, $OCH_3$, $SCH_3$, $NH_2$, Br, isopropyl, isobutyl, and secbutyl.

7. The compound according to claim 1, selected from the group consisting of:
9-(butylamino)-8H-acenaphtho[1,2-b]pyrrol-8-one;
9-(hexylamino)-8H-acenaphtho[1,2-b]pyrrol-8-one;
9-(3-phenylpropylamino)-8H-acenaphtho[1,2-b]pyrrol-8-one;
3-ethoxy-9-(3-phenylpropylamino)-8H-acenaphtho[1,2-b]pyrrol-8-one;
3-benzoyl-9-(butylamino)-8H-acenaphtho[1,2-b]pyrrol-8-one;
9-(butyl(methyl)amino)-8H-acenaphtho[1,2-b]pyrrol-8-one;
3-(4-bromophenylthio)-9-(butylamino)-8H-acenaphtho[1,2-b]pyrrol-8-one;
3-(4-bromophenylthio)-9-(3-phenylpropylamino)-8H-acenaphtho[1,2-b]pyrrol-8-one;
9-(butylamino)-3-thiomorpholino-8H-acenaphtho[1,2-b]pyrrol-8-one;
9-(3-phenylpropylamino)-3-thiomorpholino-8H-acenaphtho[1,2-b]pyrrol-8-one;
9-(butylamino)-3-(4-isopropylphenoxy)-8H-acenaphtho[1,2-b]pyrrol-8-one; and
3-(4-isopropylphenoxy)-9-(3-phenylpropylamino)-8H-acenaphtho[1,2-b]pyrrol-8-one.

8. A method of preparing the compounds of claim 1, comprising a step of reacting compounds of Formula i with $NH_2CHR^2R^3$ under room temperature for 0.5 to 0.8 hr,

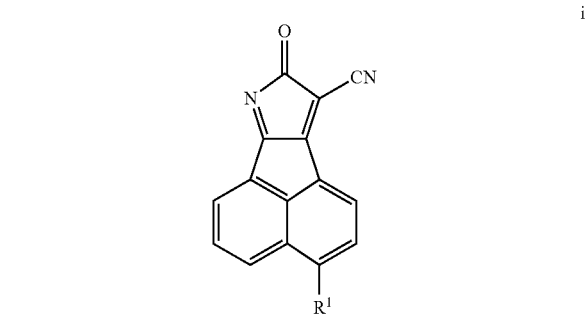

i wherein the mole ratio of compounds of Formula i to $NH_2CHR^2R^3$ is 1:5 and the solvent is acetonitrile.

9. An acenaphtho heterocyclic compound of Formula II:

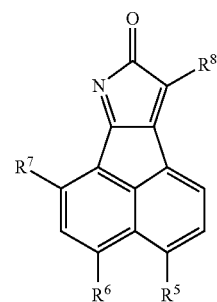

II wherein:

$R^5$ is $XR^9$, $R^6$ is H, and $R^7$ is selected from $XR^9$ and H;

$R^8$ is selected from the group consisting of CN, COOH, $COOR^{10}$, and $CONHR^{10}$;

when X is selected from the group consisting of O, carbonyl, ester, amide, and sulfamide, $R^9$ is selected from $(CH_2)_nY$ and $(CH_2)_nPh$-(o,m,p)Y, wherein Y is selected from the group consisting of straight or branched $C_{2-8}$ alkyl, and straight or branched $C_{1-8}$ alkyl substituted by halogen, amino, hydroxyl, ester or carboxyl; $R^{10}$ is a straight or branched $C_{1-6}$ alkyl that is unsubstituted or substituted by halogen, amino, hydroxyl, ester, carboxyl or $(CH_2)_nPh$-(o,m,p)Z; and Z is selected from the group consisting of $CH_3$, $C_2H_5$, $NO_2$, Ph, F, Cl, Br, $CF_3$, $OCH_3$, $SCH_3$, $NH_2$, and $N(CH_3)_2$;

when X is S, $R^9$ is $(CH_2)_nPh$-(o,m,p)Y, wherein Y is selected from the group consisting of straight or branched $C_{2-8}$ alkyl, and straight or branched $C_{1-8}$ alkyl substituted by halogen, amino, hydroxyl, ester or carboxyl;

$R^{10}$ is straight or branched $C_{1-6}$ alkyl that is unsubstituted or substituted by halogen, amino, hydroxyl, ester, carboxyl or $(CH_2)_nPh$-(o,m,p)Z; and Z is selected from the group consisting of $CH_3$, $C_2H_5$, $NO_2$, Ph, F, Cl, Br, $CF_3$, $OCH_3$, $SCH_3$, $NH_2$, and $N(CH_3)_2$;

n is 0 to 4.

10. The compound according to claim 9, wherein $R^8$ is CN.

11. The compound according to claim 10, wherein $R^9$ is $(CH_2)_nPh$-(o,m,p)Y.

12. The compound according to claim 11, wherein X is O or S and Y is a straight or branched $C_{3-5}$ alkyl.

13. The compound according to claim 12, wherein Y is selected from isopropyl, isobutyl or secbutyl.

14. The compound according to claim 9, selected from the group consisting of:
   3-(4-sec-butylphenoxy)-8-oxo-8H-acenaphtho[1,2-b]pyrrole-9-carbonitrile;
   4-(4-sec-butylphenoxy)-8-oxo-8H-acenaphtho[1,2-b]pyrrole-9-carbonitrile;
   3-(4-isobutylphenoxy)-8-oxo-8H-acenaphtho[1,2-b]pyrrole-9-carbonitrile;
   4-(4-isobutylphenoxy)-8-oxo-8H-acenaphtho[1,2-b]pyrrole-9-carbonitrile;
   3-(4-isopropylphenoxy)-8-oxo-8H-acenaphtho[1,2-b]pyrrole-9-carbonitrile;
   3-(4-isobutylphenylthio)-8-oxo-8H-acenaphtho[1,2-b]pyrrole-9-carbonitrile;
   4-(4-isobutylphenylthio)-8-oxo-8H-acenaphtho[1,2-b]pyrrole-9-carbonitrile;
   3-(4-isopropylphenylthio)-8-oxo-8H-acenaphtho[1,2-b]pyrrole-9-carbonitrile; and
   3-(4-sec-butylphenylthio)-8-oxo-8H-acenaphtho[1,2-b]pyrrole-9-carbonitrile.

15. A method of preparing the compounds of claim 9, comprising step a or step b:

a. reacting 8-oxo-8H-acenaphtho[1,2-b]pyrrole-9-carbonitrile with a nucleophilic reagent selected from alcohol, phenol, ester or amide, under 20-100° C. for 0.5-24 hours, after vaporizing the solvent, separating by chromatography to obtain 3-, 6- or 3,6-substituted 8-oxo-8H-acenaphtho[1,2-b]pyrrole-9-carbonitrile, and hydrolyzing said carbonitrile and esterifing or amidating thereafter to obtain a compound of claim 9;

b. adding liquid bromine into acenaphthenequinone and refluxing for 2 hours to obtain a brominated acenaphthenequinone, reacting the brominated acenaphthenequinone with alcohol, phenol, ester or amide to obtain a corresponding substituted acenaphthenequinone, then reacting the substituted acenaphthenequinone with acetonitrile in the presence of a gel silica to obtain the compounds of Formula ii or iii;

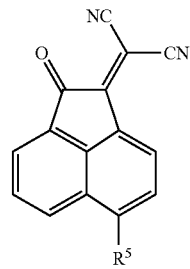

ii

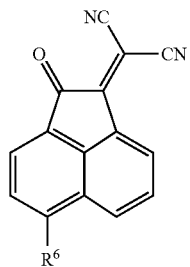

iii refluxing the compounds of Formula II or iii with acetonitrile for 0.5-6 hours in presence of $K_2CO_3$, after cooling, vaporizing some solvent under decompression conditions and filtering or column-chromatographic separating to obtain 3- or 4-monosubstituted oxy-8-oxo-8H-acenaphtho[1,2-b]pyrrole-9-carbonitrile, and hydrolyzing carbonitrile and esterifing or amidating thereafter to obtain a compound of claim 9.

* * * * *